(12) United States Patent
Carpenter et al.

(10) Patent No.: US 11,957,485 B2
(45) Date of Patent: Apr. 16, 2024

(54) HAT AND MONITORING SYSTEM

(71) Applicants: SUREPULSE MEDICAL LIMITED, Derby (GB); THE UNIVERSITY OF NOTTINGHAM, Nottingham (GB)

(72) Inventors: James Carpenter, Derby (GB); Barrie Hayes-Gill, Derby (GB); Caroline Henry, Derby (GB); Don Sharkey, Derby (GB); Lara Shipley, Derby (GB)

(73) Assignees: SUREPULSE MEDICAL LIMITED, Derby (GB); THE UNIVERSITY OF NOTTINGHAM, Nottingham (GB)

( * ) Notice: Subject to any disclaimer, the term of this patent is extended or adjusted under 35 U.S.C. 154(b) by 917 days.

(21) Appl. No.: 16/082,105

(22) PCT Filed: Mar. 3, 2017

(86) PCT No.: PCT/GB2017/050582
§ 371 (c)(1),
(2) Date: Sep. 4, 2018

(87) PCT Pub. No.: WO2017/149325
PCT Pub. Date: Sep. 8, 2017

(65) Prior Publication Data
US 2020/0281526 A1 Sep. 10, 2020

(30) Foreign Application Priority Data
Mar. 4, 2016 (GB) ..................... 1603793

(51) Int. Cl.
*A61M 16/00* (2006.01)
*A61B 5/00* (2006.01)
(Continued)

(52) U.S. Cl.
CPC .......... *A61B 5/6803* (2013.01); *A61B 5/0006* (2013.01); *A61B 5/02416* (2013.01);
(Continued)

(58) Field of Classification Search
CPC .......... A61M 16/0622; A61M 16/0057; A61M 16/0066; A61M 16/06; A61M 16/0611;
(Continued)

(56) References Cited

U.S. PATENT DOCUMENTS

| 1,268,614 A | 6/1918 | Rand |
| 2,367,074 A | 1/1945 | Turchin |

(Continued)

FOREIGN PATENT DOCUMENTS

| AU | 2014101151 A4 | 12/2014 |
| CN | 101873811 A | 10/2010 |

(Continued)

OTHER PUBLICATIONS

International Search Report from corresponding PCT Application No. PCT/GB2017/050582, dated Aug. 4, 2017.
(Continued)

*Primary Examiner* — Joseph A Stoklosa
*Assistant Examiner* — Brian M Antiskay
(74) *Attorney, Agent, or Firm* — Grossman, Tucker, Perreault & Pfleger PLLC; Donald J. Perreault

(57) ABSTRACT

A hat (200) for a neonate (120) comprising: a central portion (201), a first side portion (202) and second side portion (203) attached to opposite sides of the central portion (201), a first fastener (208); a top flap (204) and a second fastener (211). The hat (200) has an unfolded configuration and a worn configuration. In the unfolded configuration the first and second portions (202, 203) extend away from each other from the central portion (201) in opposite directions. In the worn configuration the hat (200) wraps a neonate's head with the central portion (201) in contact with the back of the neonate's head, the first portion (202) wrapped around a first side of the neonate's head and the second portion (203) wrapped around a second side of the neonate's head. The (Continued)

first and second portions (202, 203) are configured to be fastened together in the worn configuration by the first fastener (208) so that the first portion (202), central portion (201) and second portion (203) together define a hat (214) rim encircling the neonate's head. The top flap (204) is configured to cover the top of the neonate's head in the worn configuration. The top flap (204) is configured to be fastened to at least one of the first, central and second portions (202, 201, 203) by the second fastener (211). The hat (200) further comprises an optical physiological sensor that comprises: a flexible circuit board, a light emitter (310) and a light detector (311); the flexible circuit board having: a sensor portion (302) to which the light emitter (310) and light detector (311) are connected; a module portion (305) including contacts (304) for electrically connecting the light emitter (310) and light detector (311) to a removable readout module (400); and an elongate lead portion (301) between the sensor portion (302) and module portion (305).

22 Claims, 17 Drawing Sheets

(51) Int. Cl.
| | | |
|---|---|---|
| *A61B 5/024* | (2006.01) | |
| *A61B 5/05* | (2021.01) | |
| *A61B 5/1455* | (2006.01) | |
| *A61B 5/318* | (2021.01) | |

(52) U.S. Cl.
CPC .......... *A61B 5/14553* (2013.01); *A61B 5/318* (2021.01); *A61B 2503/045* (2013.01); *A61B 2560/0271* (2013.01); *A61B 2562/164* (2013.01); *A61B 2562/166* (2013.01); *A61B 2562/22* (2013.01)

(58) Field of Classification Search
CPC .......... A61M 16/0616; A61M 16/0683; A61M 16/0694; A61M 16/0816; A61M 16/0858; A61M 16/0875; A61M 16/20; A61M 16/0633; A61M 16/0825; A61M 16/0841; A61M 2016/0661; A61M 2016/003; A61M 2202/0225; A61M 2016/0027; A61M 2202/0208; A61M 2205/3331; A61M 2202/0085; A42B 1/00; A42B 1/006; A42B 1/04; A42B 1/06; A42B 1/201; A42B 1/22
USPC .......... 600/372, 382–393, 544–545
See application file for complete search history.

(56) References Cited

U.S. PATENT DOCUMENTS

| | | | |
|---|---|---|---|
| 3,221,345 A | | 12/1965 | Berg |
| 5,800,351 A | * | 9/1998 | Mann ..................... A61B 5/291 607/139 |
| 6,889,689 B1 | | 5/2005 | Neuman |
| 8,768,424 B2 | | 7/2014 | Crowe et al. |
| 9,202,008 B1 | | 12/2015 | Frederick et al. |
| 2004/0236226 A1 | | 11/2004 | Maki et al. |
| 2004/0244804 A1 | | 12/2004 | Olsen et al. |
| 2004/0267104 A1 | | 12/2004 | Hannula et al. |
| 2005/0280531 A1 | | 12/2005 | Fadem et al. |
| 2006/0020185 A1 | | 1/2006 | Al-Ali |
| 2006/0282001 A1 | | 12/2006 | Noel et al. |
| 2007/0186931 A1 | * | 8/2007 | Zollinger .......... A61M 16/0683 128/207.11 |
| 2009/0038055 A1 | | 2/2009 | Ferrara |
| 2010/0036275 A1 | * | 2/2010 | Alkire ................... A61B 5/291 600/383 |
| 2010/0081904 A1 | | 4/2010 | Medina |
| 2010/0249557 A1 | | 9/2010 | Besko et al. |
| 2011/0028822 A1 | * | 2/2011 | Beck ...................... A61B 5/25 600/386 |
| 2011/0098593 A1 | | 4/2011 | Low et al. |
| 2012/0017901 A1 | | 1/2012 | Mainusch et al. |
| 2012/0222678 A1 | | 9/2012 | Colbaugh |
| 2012/0296174 A1 | | 11/2012 | McCombie et al. |
| 2013/0038011 A1 | | 2/2013 | Reynolds et al. |
| 2013/0253334 A1 | | 9/2013 | Al-Ali et al. |
| 2014/0323840 A1 | * | 10/2014 | Ouwerkerk .......... A61B 5/684 600/300 |
| 2015/0099955 A1 | | 4/2015 | Al-Ali et al. |
| 2015/0308946 A1 | | 10/2015 | Duffy et al. |
| 2015/0351699 A1 | | 12/2015 | Addison et al. |

FOREIGN PATENT DOCUMENTS

| | | |
|---|---|---|
| CN | 102365108 A | 2/2012 |
| CN | 102665810 A | 9/2012 |
| CN | 204909797 U | 12/2015 |
| CN | 105559224 A | 5/2016 |
| WO | 2005120618 A1 | 12/2005 |
| WO | 2006096941 A1 | 9/2006 |

OTHER PUBLICATIONS

Written Opinion of the International Searching Authority from corresponding PCT Application No. PCT/GB2017/050582, dated Aug. 4, 2017.
English Translation of First Office Action of Chinese Application No. 2017800267531, Dated Nov. 25, 2020, 8 pages.
English Translation of Second Office Action of Chinese Application No. 2017800267531, Dated Jul. 28, 2021, 9 pages.
Extended European Search Report of European Application No. 19207849.1, dated May 28, 2020, 10 pages.
Search Report under Section 17(5) of United Kingdom Application No. GB1603793.9, dated Jun. 29, 2016, 5 pages.
Exam Report under Sections 12 & 13 of India Application No. 201827034981, dated May 31, 2021, 8 pages.

* cited by examiner

HAT AND MONITORING SYSTEM

The present invention relates to a hat for a neonate, and a monitoring system for a neonate, in particular the physiological condition of a neonate including but not limited to heart rate; breathing rate; and Oxygen Saturation SpO2).

Newborn babies and those up to 28 days of life (neonates) in the UK are generally given a bonnet or hat immediately following birth, to help them maintain an appropriate body temperature.

A number of commercially produced hats for neonates are available as part of continuous positive airway pressure (CPAP) systems. Makers include Carefusion, Fisher and Paykel, and Intersurgical. Such hats are available in a range of sizes.

One difficulty with a number of existing hats is in conveniently obtaining access to the neonate's head, for instance to perform a cranial ultrasound procedure. A further problem arises with the interaction of the hat and a CPAP mask and associated tube(s). It is necessary for the CPAP mask to be supported in the correct position on the neonate's head, for instance by a connection to a hat. Injuries can be inflicted on neonates (e.g. on the nasal septum) by an inappropriately fitted CPAP mask, so it is important to ensure that such systems are fitted appropriately.

In the UK, around 10% of newborn babies need some form of resuscitation at birth: 85,000 per year in the UK, 400,000 in the USA and at least 13,500,000 worldwide. Accurate monitoring of heart rate is vital to guide such interventions: both to identify when intervention is required, and to monitor how the newborn (neonate) is responding to the resuscitation. The stethoscope is the current standard of care for monitoring the neonate heart rate in the key moments following birth. However, the stethoscope's use is subject to delays and errors, which can ultimately have a severe impact on the future wellbeing of the child.

US2010/0249557 discloses a hat for a neonate that includes a pulse oximeter, for monitoring the heart rate of a neonate. U.S. Pat. No. 8,768,424 describes a photoplethysmography device for measuring heart rate.

According to a first aspect of the invention, there is provided a hat for a neonate comprising: a central portion; a first side portion and second side portion attached to opposite sides of the central portion; a first fastener; a top flap and a second fastener;

wherein the hat has an unfolded configuration in which the first and second portions extend away from each other from the central portion in opposite directions; and a worn configuration in which the hat wraps a neonate's head with the central portion in contact with the back of the neonate's head, the first portion wrapped around a first side of the neonate's head and the second portion wrapped around a second side of the neonate's head;

the first and second portions being configured to be fastened together in the worn configuration by the first fastener so that the first portion, central portion and second portion together define a hat rim encircling the neonate's head; and the top flap is configured to cover the top of the neonate's head in the worn configuration, with the top flap being configured to be fastened to at least one of the first, central and second portions by the second fastener.

The term neonate may refer to an infant that is less than four weeks old.

The unfolded configuration of the hat makes it easy to put on a neonate, for example by placing the neonate's head on the central portion (with the hat in an unfolded configuration) and wrapping the hat around the head.

In some embodiments the central portion can be pulled backwards to reveal the fontanelle to allow access for scanning and other medical procedures.

The hat may be substantially T-shaped when in an unfolded configuration, with the top flap being connected to the central portion.

The first and second portions may be configured to overlap on the neonate's forehead when fastened together by the first fastener.

The first fastener and/or the second fastener may comprise a hook and loop fastener. Hook and loop fasteners are quick and easy to fasten and unfasten, and provide reliable and secure attachment (especially, but not exclusively, in the context of a single use item).

In some embodiments the loop portion of the first fastener and/or second fastener may be provided by a fabric from which the hat is made, rather than by a patch of loop material attached to the fabric. This may give more flexibility in where the fastener can be attached.

The first fastener may be configured to provide a plurality of fastening positions so as to allow a range of adjustment of the length of the hat rim, so as to accommodate a range of neonate head sizes.

The range of adjustment may be at least 1 cm, or at least 0.5 cm, or 2 cm.

The hat may further comprise a strap for supporting a continuous tube (e.g. a continuous airway pressure or CPAP tube) adjacent to the neonate's forehead when the first, central and second portions encircle the neonate's head.

The strap may comprise an elastic fabric material. The strap may comprise a strap fastener, for fastening the strap to at least one of the first and second portions.

The strap may be fixed at one end to one of the first or second portion, and the other end of the strap may be securable to the other of the first or second portions using the strap fastener. The detachable strap may be securable to either the first or second portions via hook and loop attachments.

The strap may comprise a friction enhancing lining on an inner surface thereof. The friction enhancing lining may comprise silicone rubber.

The hat may comprise a first plurality of eyelets in the first portion adjacent to the hat rim, and a second plurality of eyelets in the second portion adjacent to the hat rim. The first and second plurality of eyelets may be for securing a CPAP mask to the neonate's face using CPAP cords that thread into the eyelets. The plurality of eyelets in each of the first and second portion may provide a range of CPAP mask securing locations or endotracheal tube securing locations, or securing locations for other fittings.

The eyelets may be strengthened by stitching a hem around each eyelet. This may provide a firm fixation point for the securing tethers of either a CPAP mask or endotracheal tube.

The hat may comprise at least one external loop through which a tube (such as a CPAP tube, or an intubation tube) may be supported adjacent to the exterior of the hat.

The at least one external loop may comprise a first and second external loop, arranged to be positioned on either side of the neonate's forehead when the hat is worn.

The hat may comprise a first dart between the first and central portion and a second dart between the second and central portion. A third dart may be provided in the central portion, the third dart arranged to improve the conformation of the central portion with the back of the neonate's head.

The first and second dart may extend substantially toward the rim from a top edge of the hat, the top edge being on the opposite side of the hat to the hat rim.

The second fastener may comprise a plurality of fastening locations spaced around the perimeter of the top flap.

The first, second, and central portions, and the top flap, may be substantially formed from a fabric material.

The fabric material may be stretchable substantially in one direction only. The direction may be along the circumference. This enables the hat to provide a comfortable fit, while accommodating a range of head sizes and shapes.

The fabric may have at least an inner ply and an outer ply. The inner ply may be larger in extent than the outer ply (or the outer ply may be larger than the inner ply). The outer ply may be provided in regions of the inner ply.

According to an aspect of the invention, there is provided a hat for a neonate comprising an inner fabric ply and an outer fabric ply, a first hole through the inner fabric ply at a first location and a second hole through the outer fabric ply at a second location, wherein, when the hat is worn by a neonate, the first location is adjacent to the forehead and the second location is adjacent to the rear of the head, the first and second hole allowing an optical physiological sensor lead to be threaded through a space between the inner and outer plies between the first and second holes. The inner ply may be larger in extent than the outer ply (or the outer ply may be larger than the inner ply). The outer ply may be provided in regions of the inner ply.

The inner ply may comprise a material that is stretchy in a single direction. The outer ply may comprise a hook accepting material (for a hook and loop fastener).

The optical physiological sensor may comprise at least one of: an optical heart-rate sensor, a pulse oximeter, and optical breathing sensor, an optical blood flow sensor, or any other optical physiological sensor.

The hat of the first aspect may further comprise an inner hole through the inner fabric ply at a first location and an outer hole through the outer fabric ply at a second location. The first location may be in one of the first portion and second portion. The second location may be in the central portion or the other of the first and second portion. The inner and outer hole may allow an optical physiological sensor lead to be threaded through a space between the inner and outer plies between the inner and outer holes.

The inner hole may be a first inner hole, and the hat may further comprise a second inner hole through the inner fabric ply, spaced apart from the first inner hole by 0.5 cm to 3 cm.

The inner holes may be through the inner fabric ply and not the outer fabric ply.

The outer hole may be a first outer hole, and the hat may further comprise a second and third outer hole disposed between the inner hole and the first outer hole.

The outer holes may be through the outer fabric ply and not the inner fabric ply.

The second and third outer holes may be spaced apart from each other by between 0.5 cm and 3 cm.

The second and third outer holes may be arranged to allow an optical physiological sensor lead to be threaded between the second and third outer holes, so as to enable the optical physiological sensor lead to be cut between the second and third outer holes while the hat is worn. The physiological sensor may then be conveniently removed from the hat.

According to a second aspect, there is provided an optical physiological sensor comprising: a flexible circuit board, a light emitter and a light detector;

the flexible circuit board having:

a sensor portion to which the light emitter and light detector are connected;

a module portion including contacts for electrically connecting the light emitter and light detector to a readout module; and an elongate lead portion between the sensor portion and module portion.

The elongate lead portion may be flexible.

The light emitter may comprise a plurality of light emitting elements.

The sensor portion may comprise a package that includes both the light emitter and light detector.

The light emitter may comprise a light emitting element with a first output wavelength, and a light emitting element with a second, different output wavelength.

The light emitter may further comprise a light emitting element with a third output wavelength, different from the first and second output wavelengths. The light emitter may further comprise a light emitting element with a fourth output wavelength, different from the first, second and third output wavelengths.

The flexible circuit board may include a tang extending away from the sensor portion in a different direction to the lead. The tang may extend in a direction at 180 degrees to the lead, or at another angle.

The light detector may be a single photodetector or an array of detectors in the form of a multi-pixel camera. The light detector may be operable to detect wavelengths within and/or outside the visible spectrum.

The tang may be an elongate member. The tang may extend away from the sensor portion at an angle of between 135 and 155 degrees from the lead, or between 170 and 190 degrees from the lead (e.g. at substantially 180 degrees from the lead).

The tang may comprise at least one lateral projection or recess configured to assist in preventing withdrawal of the tang through a hole (e.g. the second inner hole). The tang may comprise a barbed or hammerhead shaped structure, with a sloped edge to enable the tang to be inserted through a hole (e.g. the second inner hole), and a lateral edge (substantially perpendicular to a direction of insertion) for inhibiting withdrawal of the tang from the hole in which it is inserted. The tang may comprise a substantially circular or spherical 'blob' for assisting in retaining the tang in the hole. The applicant has found that a curved feature (e.g. a curved projection) may make removal of the tang easier, at the same time as providing an acceptable degree of retention within the hole (e.g. second inner hole)

The width of the lead may be less than 1 cm. The thickness of the lead may be less than 0.5 mm.

The module portion may comprise a substantially rigid planar element for supporting the contacts.

The module portion may comprise a ferromagnetic element.

The hat of the previous aspects may further comprise the optical physiological sensor of the second aspect.

At least part of the elongate lead portion of the optical physiological sensor may be disposed between an inner and an outer ply of the hat.

The sensor portion may be supported by the hat at an inner surface of the hat near the rim of the first portion or the second portion, such that the sensor portion is positioned on a neonate's forehead when the hat is worn.

The sensor portion may be supported between the first inner hole and the second inner hole, the first inner hole receiving the elongate lead portion, and the second inner hole receiving the tang.

The elongate lead portion may be threaded between the second and third outer holes, so as to enable the lead to be cut between the second and third outer holes while the hat is worn. The sensor portion may then be conveniently removed from the hat.

The sensor portion may comprise an transparent element, arranged to be between the light emitter and light detector, and the skin, in use (i.e. covering the light emitter and light detector). The transparent element may be less than 1 mm thick. The transparent element may comprise silicone. The transparent element may be transparent at the wavelengths emitted by the light emitter. The thickness of the transparent element may be less than 1 mm, or less than 0.5 mm.

The transparent element may comprise a region that is adhesive or tacky to skin.

The light emitters and detectors may be separated from each other by a baffle to avoid light shunting.

The sensor portion may further comprise at least one electrode for making an electrical connection to the skin of a neonate. The at least one electrode may be a wet electrode, or may be configured for coupling to skin via a hydrogel or by capacitive coupling. The at least one electrode may be suitable for performing an ECG measurement.

The sensor portion may comprise an array of sensors, the array of sensors comprising at least one optical sensor and at least one electrode.

According to a third aspect, there is provided a readout module for an optical physiological sensor, wherein the readout module comprises:
  an electrical power store for powering the readout module;
  an electronic circuit for providing a drive signal to a light emitter of the physiological sensor and for receiving the signal from a light detector of the physiological sensor;
  a processor for processing the signal from the light detector to produce data; and
  a wireless transmitter, configured to wirelessly transmit the data from the readout module to a base station.

The readout module may be further configured to obtain an ECG measurement from the at least one electrode of the sensor module. The processor may be configured to process a signal derived from the at least one electrode to produce ECG data, and the wirelessly transmitted data may comprise ECG data.

The readout module may further comprise: a housing containing the electrical power store, the electronic circuit and the wireless transmitter, and a cradle configured to receive the housing and a module portion of an optical physiological sensor (e.g. according to a previous aspect).

The readout module may further comprise a permanent magnet for attaching a module portion of an optical physiological sensor to the readout module by attracting a ferromagnetic element of the module portion.

The readout module may further comprise a connector for engaging a plurality of electrical contacts of a module portion of an optical physiological sensor.

The connector may comprise a plurality of pogo pins.

The readout module may comprise a status indicator configured to display an indication of the status of the readout module. The status indicator may be a light emitting element. The light emitting status indicator may be configured to emit at least two different colours. The status indicator may be configured to indicate an amount of charge in the electrical power store. The status indicator may be configured to indicate a fault status.

The readout module may be waterproof according to the IPX-7 standard.

The processor may encrypt the signal from the light detector to produce encrypted raw sensor data for transmission. Alternatively the processor may be configured to process the raw data locally (e.g. in real time, or with a delay of less than 1 second) to determine at least one of: heart rate, breathing, SpO2 and other relevant physiological signals. This may allow a reduced bandwidth of data to be transmitted thereby saving power in the module.

According to a fourth aspect, there is provided a monitoring system for a neonate, comprising a readout module according to the third aspect, and the optical physiological sensor of any previous aspect.

The system may include the hat of any previous aspect.

According to a fifth aspect, there is provided a receiving station comprising a display and a docking portion for receiving a readout module of an optical physiological sensor, wherein:
  the receiving station is configured to wirelessly receive data from a readout module of an optical physiological sensor, and to display an indication of a physiological parameter (e.g. heart rate, breathing rate, SpO2, blood flow etc) of the neonate on the display;
  the docking portion comprises charging contacts by which the receiving station is operable to charge the readout module.

The receiving station may further comprise a ferromagnetic element in the docking portion, to enable a readout module to be fixed in place in the docking portion using a permanent magnet of the readout module.

The docking portion may be a first docking portion, and the receiving station may comprise a second docking station for receiving and charging a second readout module.

The receiving station may further comprise an indicator operable to provide a visual indication every 6 seconds.

The indicator may comprise a light source (e.g. an LED) configured to flash or change state every 6 seconds. For example, the indicator could stay on for 6 seconds, then go off for 6 seconds, or briefly illuminate every 6 seconds.

The indicator may be used to improve the accuracy of a stethoscope reading of heart rate. At present, the clinician taking a stethoscope heart rate must count a 6 second interval at the same time as counting the heart beats (which can be cognitively challenging). The accuracy of a clinician's stethoscope reading may be improved with the use of the timing indicator.

The receiving station may further comprise non-volatile data storage. The receiving station may be configured to store data from the readout module of the optical physiological sensor and/or a time history of the physiological parameter.

The receiving station may be configured to process the data from the readout module of the optical physiological sensor to determine at least one of: heart rate, breathing rate, SpO2, and blood flow.

The receiving station may be configured to use the display to indicate at least one of: heart rate, breathing rate, SpO2, and blood flow.

According to a sixth aspect, there is provided a monitoring system for a neonate comprising the receiving station of the fifth aspect, and a readout module according the third aspect. The monitoring system may include the hat of any previous aspect.

Any of the features of any aspect may be combined with any other aspect, including the optional features.

Embodiments of the invention will be described, purely by way of example, with reference to the accompanying drawings, in which.

Figure 1:
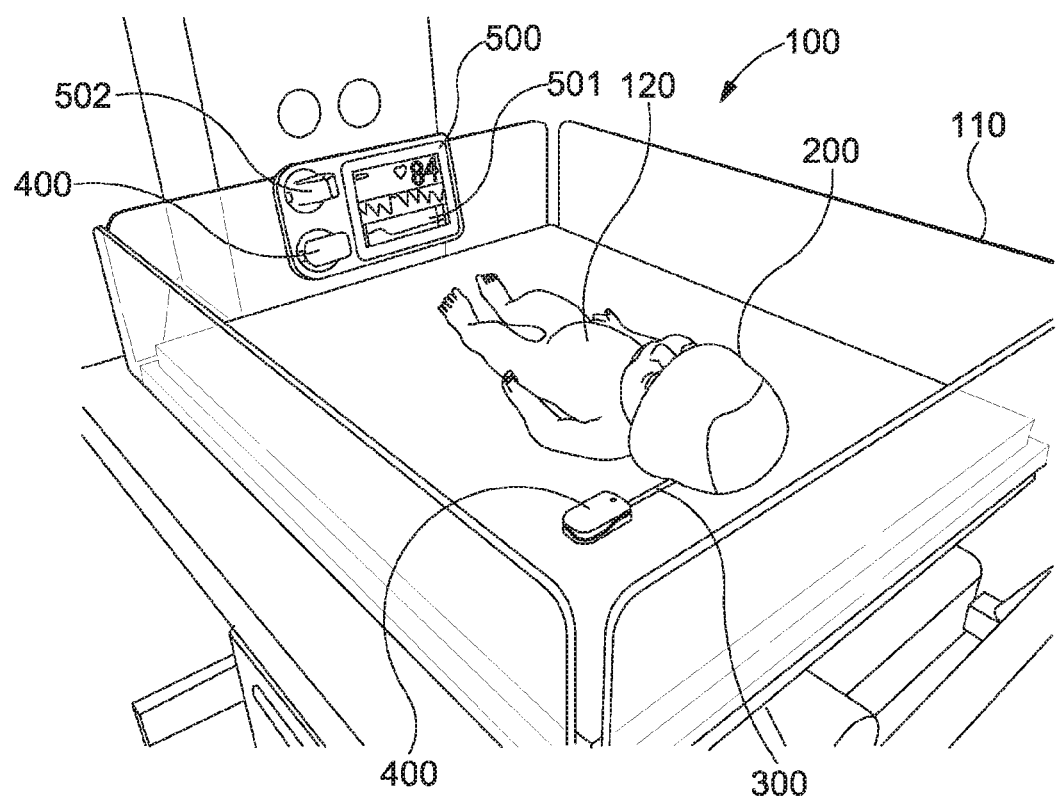
FIG. 1 is a view of a system according to an embodiment.

Referring to FIG. 1 a system 100 for neonatal physiological monitoring is shown, comprising: a hat 200, optical physiological sensor 300, readout module 400 and base station 500.

The hat 200 is worn by a neonate 120, with the neonate lying on a resuscitaire 110. The optical physiological sensor 300 is supported by the hat 200 adjacent to the skin of the neonate 120, so as to monitor the physiological signals of the neonate 120. The optical physiological sensor 300 includes a lead, connecting a light emitter(s) and light detector(s) of the optical physiological sensor 300 to a readout module 400. The readout module 400 provides drive signals to the light emitter(s), and receives signals from the light detector (s). The readout module 400 comprises a wireless transmitter, configured to transmit data (either raw physiological or processed physiological data) derived from the light detector (s) signals (e.g. heart rate, breathing rate, SpO2, blood flow, etc) to the base station 500. The base station 500 is configured to receive the data from the readout module 300, and to display physiological signals of the neonate.

Figure 2:
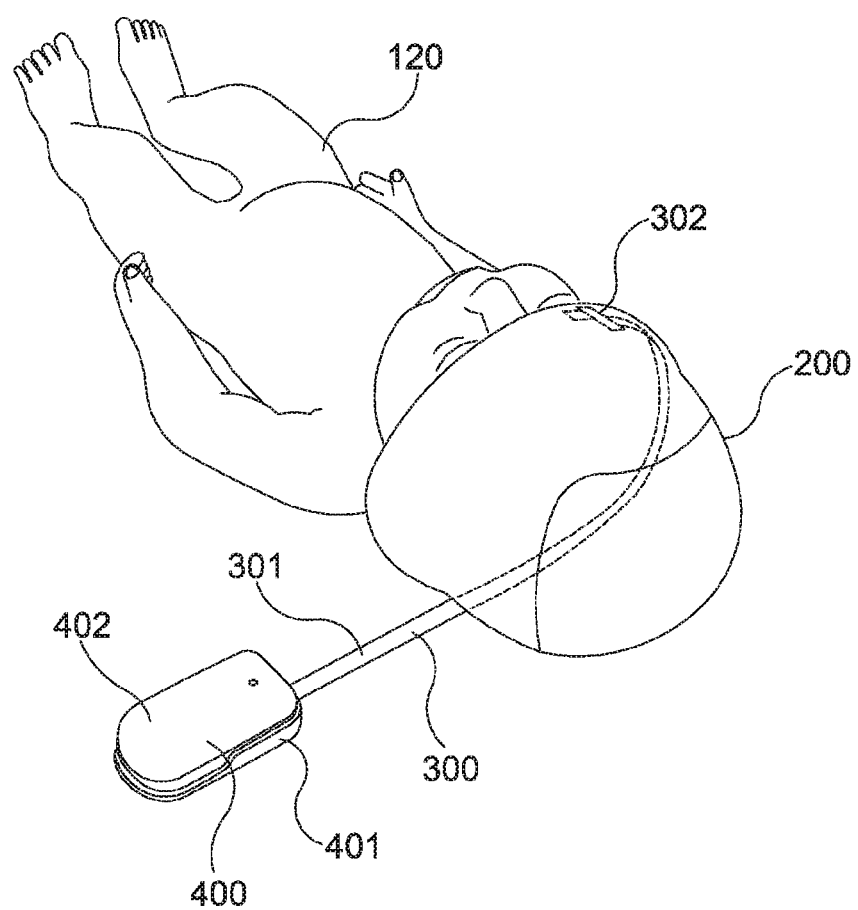
FIG. 2 is a view of a neonate wearing a hat according to an embodiment.

As shown in FIG. 2 the hat 200 supports a sensor portion 302 of the optical physiological sensor 300 adjacent to the skin of the neonate 120, so as to enable a physiological signal measurement. The sensor portion 302 is preferably supported adjacent to the forehead of the neonate 120, which is a good location to perform measurements.

A pressure indicator may be woven into the fabric that indicates if the hat is too tight. The pressure indicator may comprise a region of zig zag stitching, the length of which indicates an amount of extension (strain) of the fabric. The pressure indicator may indicate that the hat is too tight when the pressure indicator exceeds a predetermined length (e.g. 1 cm). This may ensure that the hat does not cause any facial congestion or oedema or worsen any existing facial oedema.

The elongate lead may be formed into a curved region, arranged to conform more easily with the curvature of the head. This may ensure that the elongate lead follows the contours of the baby's head, reducing the likelihood of pressure damage. The optical physiological sensor 300 (examples of which will be described in more detail later) includes an elongate lead 301 connecting a module portion of the sensor 300 (for connection to the readout module 400) to the sensor portion 302. The hat 200 may be configured to support the lead 301 against the opposite side of the neonate's head to the readout module 400, so that the lead 301 passes under the neonate's head on its way to the readout module 400. This configuration helps to limit any movement of the sensor portion 302 relative to the neonate's head, resulting in improved reliability and accuracy of performing the optical physiological measurement (e.g. a photoplethysmogram measurement).

Figure 3:
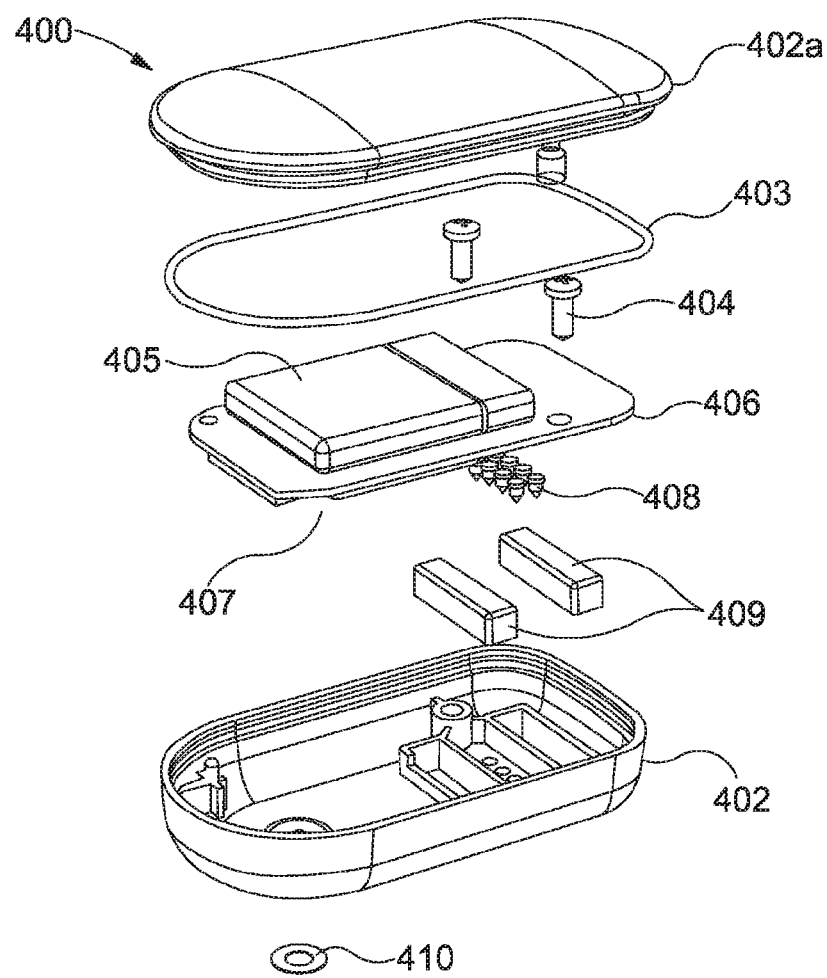
FIG. 3 is an exploded diagram of a readout module according to an embodiment.

FIG. 3 is an exploded diagram of a readout module 400 according to an embodiment. In this example, the readout module 400 comprises: an upper housing 402a, a lower housing 402b, a seal element 403, fasteners 404, electrical power store/battery 405, readout circuit board 406, readout circuit (including processor, power management, LED drive, detection circuit and wireless transmitter) 407 (on the reverse side of the readout circuit board 406), connectors 408, permanent magnets 409 and an optional semi-permeable membrane 410.

The upper housing 402a and lower housing 402b engage with each other (e.g. by a snap fit), and together define a housing of the readout module 400. The seal element 403 ensures that the housing is waterproof, for example to IPX7 standard. The optional semi-permeable membrane 410 may comprise a gas permeable hydrophobic membrane such as Gore-Tex®, so as to allow any undesirable chemical gases or vapours within the housing 402 to escape while maintaining a waterproof housing.

The readout circuit board 406 is secured to the lower housing 402b by two screw type fasteners 404. On one side of the readout circuit board 406 is an electrical power store 405, which may be re-chargeable. The power store 405 may comprise a re-chargeable battery (e.g. lithium-ion), or a supercapacitor. On the reverse side of the readout circuit board 406 is disposed an electrical circuit 407. The electrical circuit 407 is configured to provide output signals for driving a light emitter 310 of an optical physiological sensor 300, and to readout signals from a light detector 311 of the optical physiological sensor 300. In noise challenged environments the light emitter 310 can be driven in a modulated fashion and the detector 311 operated in a heterodyne lock in mode. There may be a plurality of light detectors 311 and light emitters 310.

The readout circuit 407 may be configured in accordance with the teaching of U.S. Pat. No. 8,768,424. In some embodiments, the readout circuit 407 may comprise a processor, configured to process signals from the light detector 311 to determine at least one of: heart rate and a level of blood oxygen saturation, breathing rate and blood flow. Alternatively, the readout circuit 407 may transmit data in a more raw form to the receiving station 500, and the receiving station may process the data to determine at least one of heart rate, a level of blood oxygen saturation, breathing rate, blood flow and ECG measurement.

Modulation of the light emitters may be necessary to avoid noise (both optical and electrical) but also to separate the different wavelengths deployed. To strengthen the selectivity a bandpass filter can be deployed before the ADC and subsequent digital lock in. Alternatively an analogue demodulator such as a Gilbert cell and low pass filter can be deployed in the analogue detection path.

In another electronic design implementation, the wavelengths can be transmitted in a time division multiplexing format (effectively DC version) and ambient background can be removed by the transmission of a null signal.

The readout module 400 may comprise a pair of permanent magnets 409, which are used to maintain engagement between the readout module 400 and the receiving station 100 (e.g. during charging), and between the connectors 408 of the readout module 400 and contacts of a module portion 305 of the optical physiological sensor 300.

The connectors 408 may comprise at least one pogo-pin type connector. Pogo pin connectors comprise a telescopic sprung contact, for making reliable contact without the need for a plug type connector. The pogo-pins may be arranged in a rectangular or circular array.

The readout module 400 may be configured to obtain an ECG measurement from at least one electrode in contact with the skin of the neonate.

FIGS. 4 to 14 each show various views of hats according to embodiments of the invention. Although there are differences between the embodiment shown in FIGS. 4, 5 and 6, the embodiment shown in FIGS. 8 and 9, the embodiment shown in FIGS. 10 and 11, and the embodiment shown in FIGS. 12 and 13, a large number of features are common to each. The description below relates to each of the example embodiments unless otherwise noted.

The hat 200 is configured to wrap around a neonate's head, with the central portion 201 in contact with the back of the neonate's head. The first portion 202 is arranged to wrap around a first side and the forehead of the neonate's head, and is configured to carry a sensor portion 302 of an optical physiological sensor 300.

Figure 6:
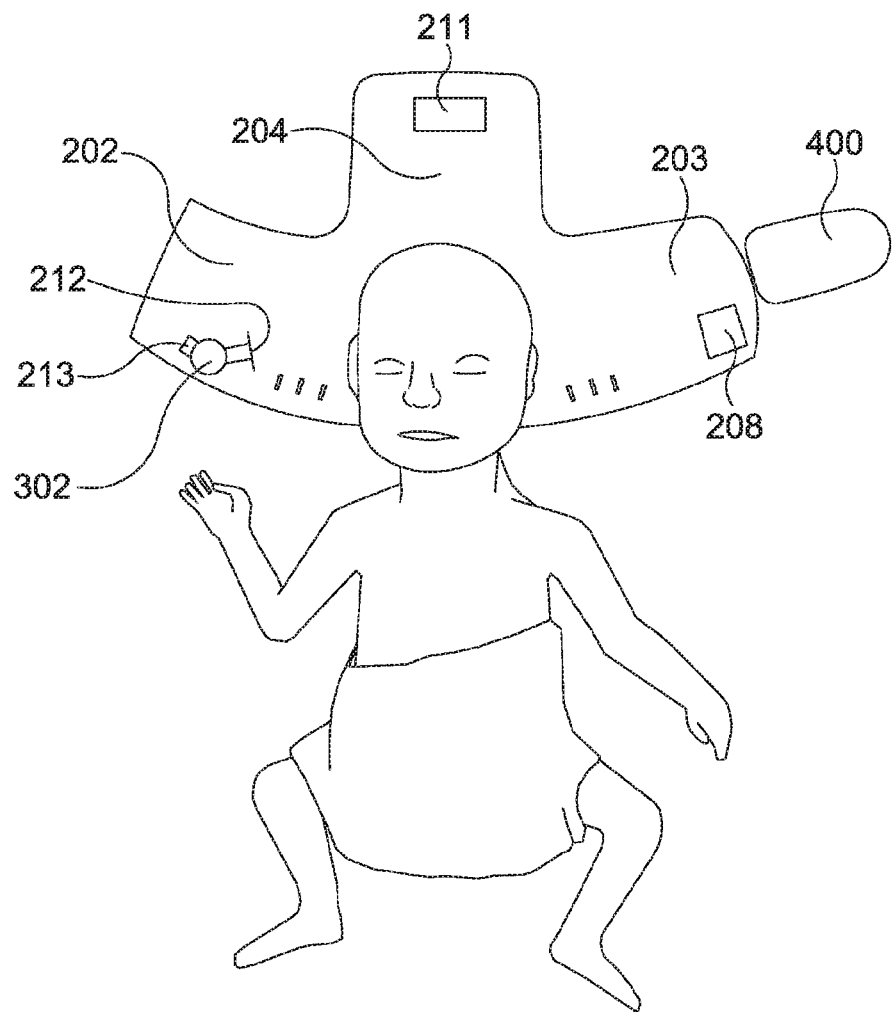
FIG. 6 is a view of the hat of FIG. 4 with a neonate positioned on the central portion of the hat, ready for the hat to be wrapped around the neonate's head.
Figure 7:
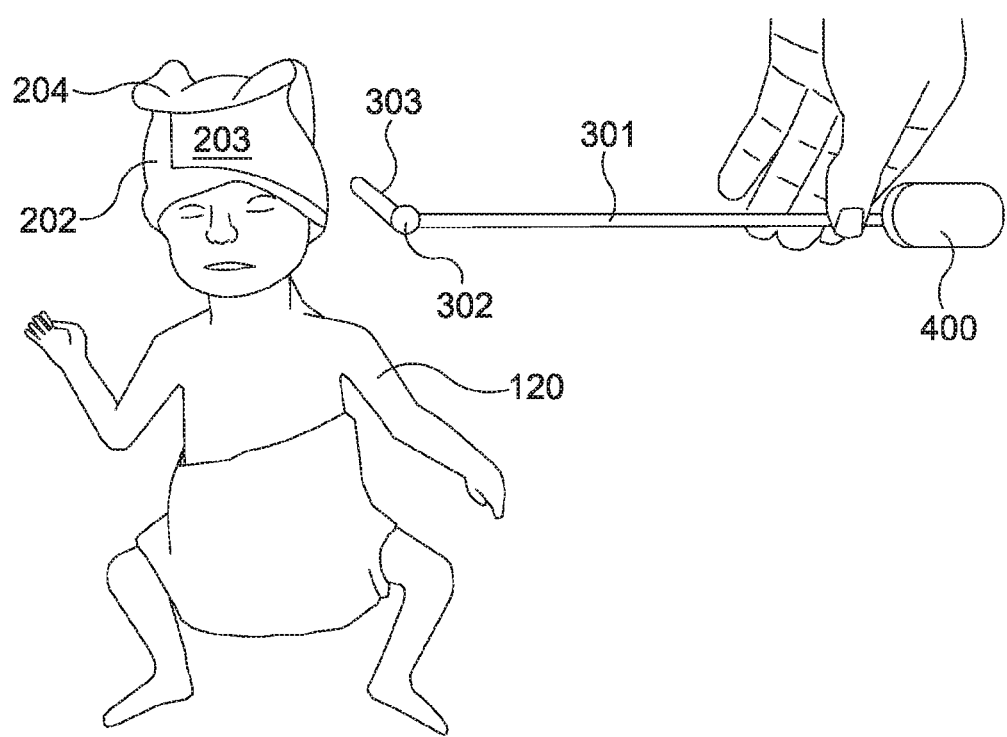
FIG. 7 is a view of the hat of FIG. 4 in a worn configuration on the head of a neonate, also showing an optical physiological sensor and associated readout module.
Figure 10:
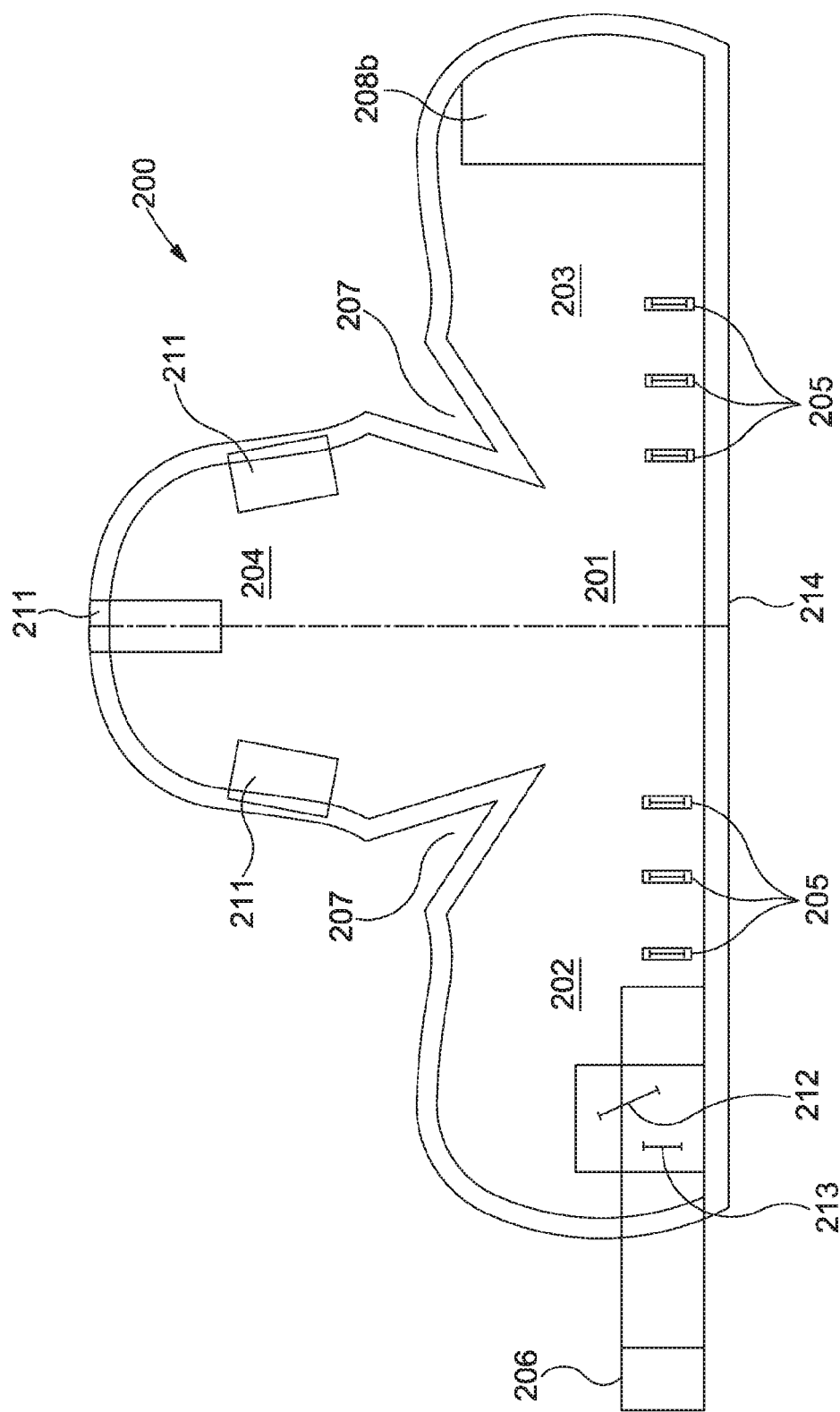
FIG. 10 is a diagram of the inner side of a hat according to a further embodiment.

As can most clearly be seen in FIG. 6, the hat 200 is arranged to bring the sensor portion 302 into contact with the forehead of a neonate 120 when the hat 200 is worn. The second portion 203 is arranged to wrap around the second side and the forehead of the neonate's head, overlapping with the first portion 202, so as to encircle the neonate's head with the first, central and second portions 201, 202, 203 (as shown in FIGS. 7 and 10).

Figure 8:
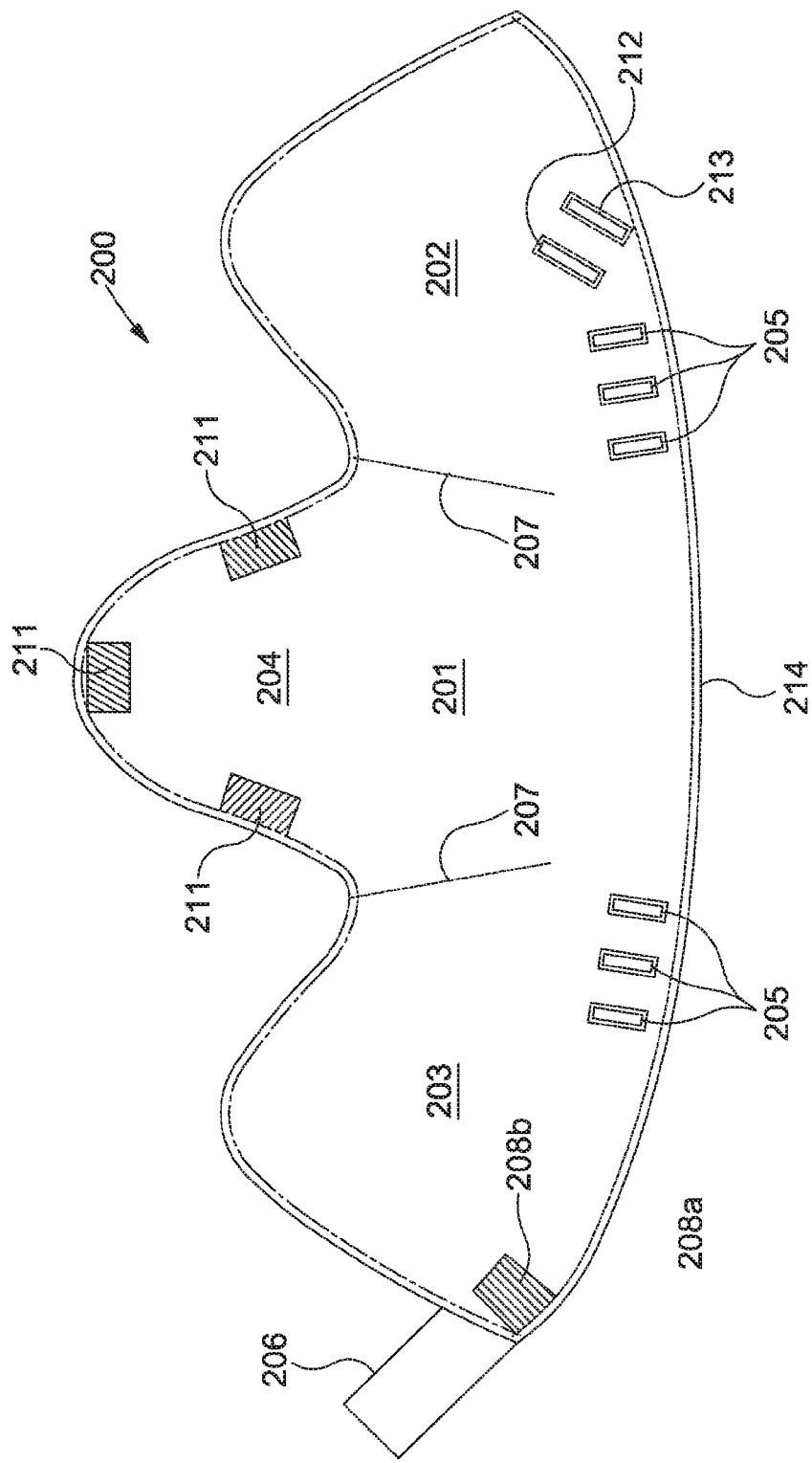
FIG. 8 is a diagram of the inner side of a hat according to an embodiment.
Figure 9:
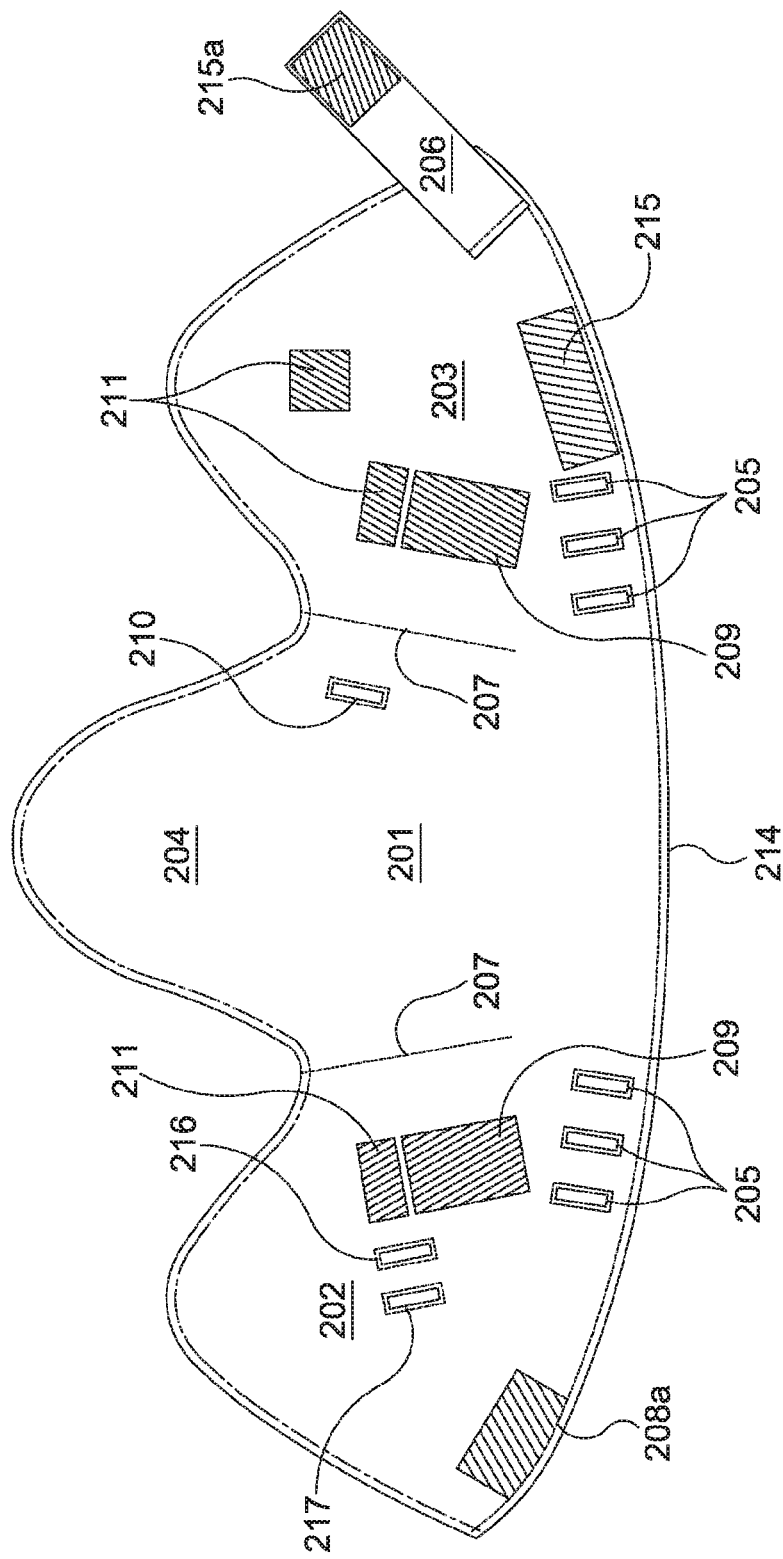
FIG. 9 is a diagram of the outer side of the hat of FIG. 8.

The hat 200 comprises a first fastener 208 arranged to fasten the first and second portions 202, 203 together in the worn position. The first fastener 208 may be any suitable fastener (e.g. button, popper, etc), but preferably comprises a hook and loop type fastener. For instance, the first fastener 208 may comprise a hook portion 208a on an outer side of the first portion 202, and a loop portion 208b on an inner side of the second portion 203 (as shown in FIGS. 8 and 9).

Figure 12:
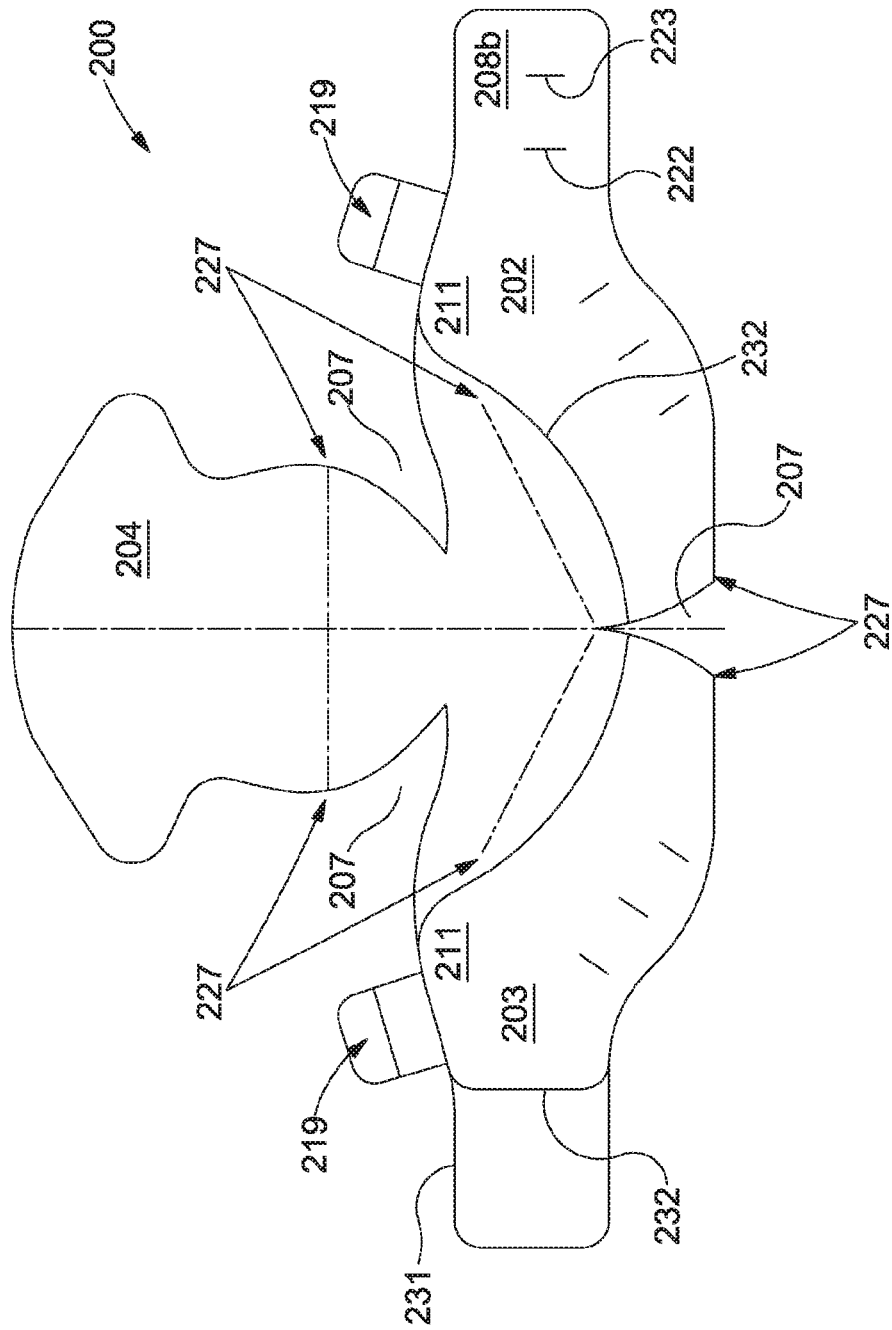
FIG. 12 is a diagram of the inner side of a hat according to an embodiment.
Figure 13:
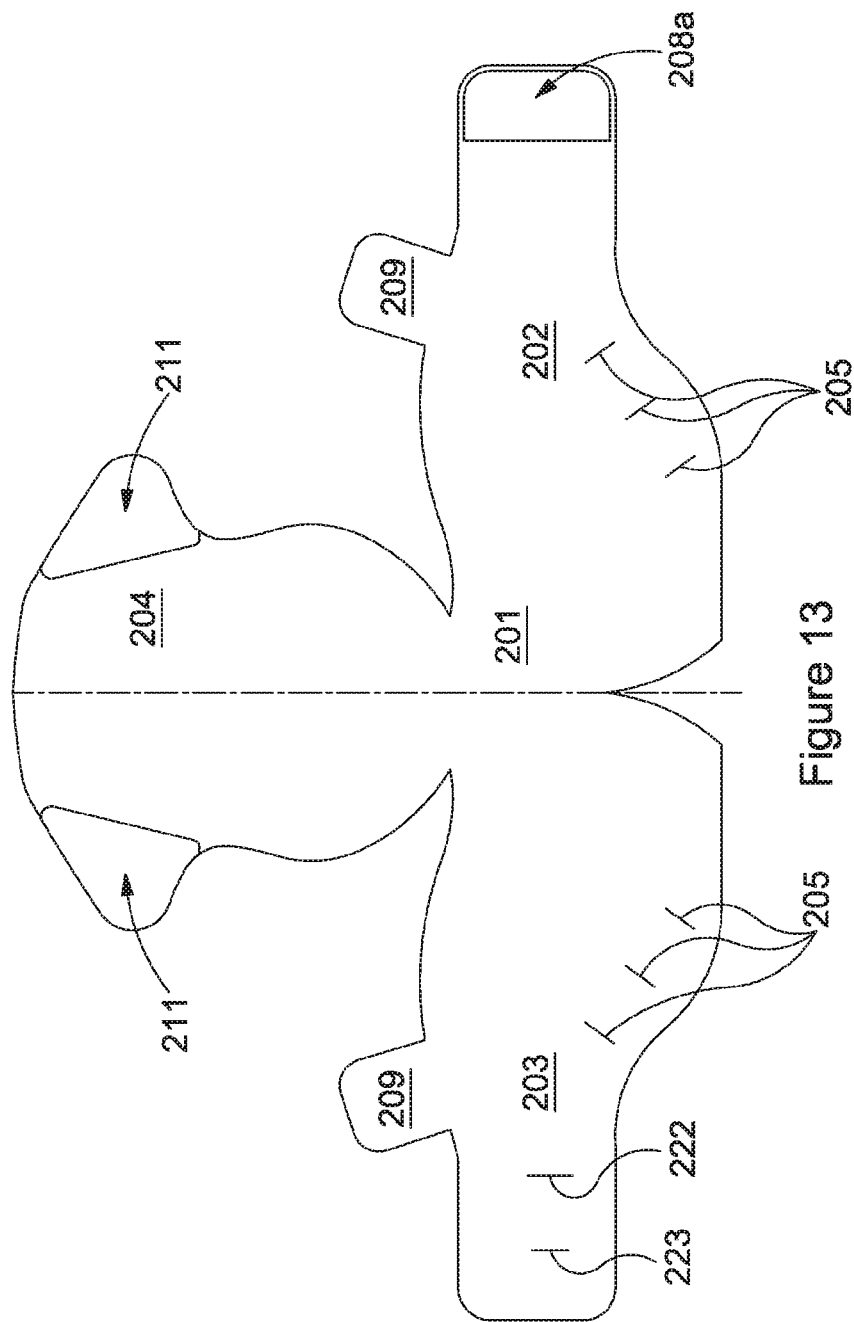
FIG. 13 is a diagram of the outer side of a hat according to an embodiment.

In each example fastener described herein, the location of the hooks and loops can be reversed. For example, for the first fastener 208, a hook portion may be located on the first or second portion, and the corresponding loop portion may be located on the other of the first or second portion. In some embodiments a loop portion of a fastener may be provided by a fabric from which the hat is made, without the need for a patch of a specific loop material. For example, the first fastener 208 may comprise a hook portion 208a on an outer side of the second portion 203, and a corresponding loop portion 208b on an inner side of the first portion 202 (as shown in FIGS. 12 and 13).

Figure 4:
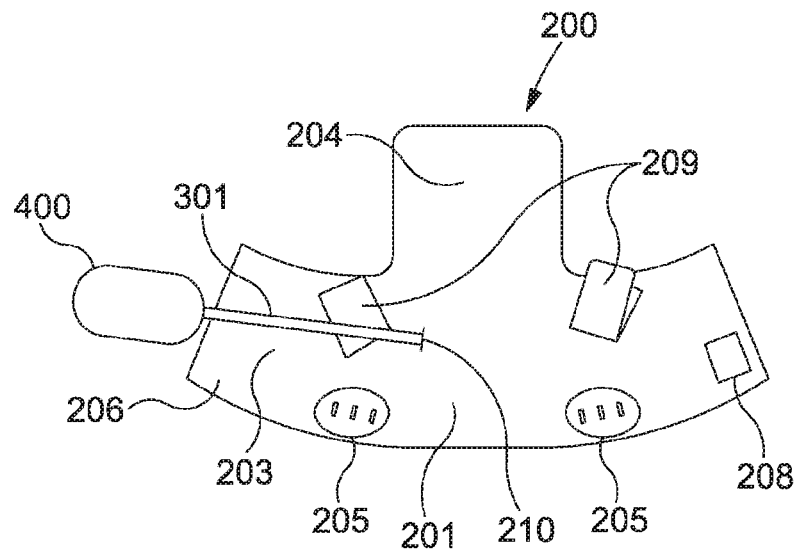
FIG. 4 is a view of a hat according to an embodiment in an unfolded configuration from the exterior side of the hat.
Figure 5:
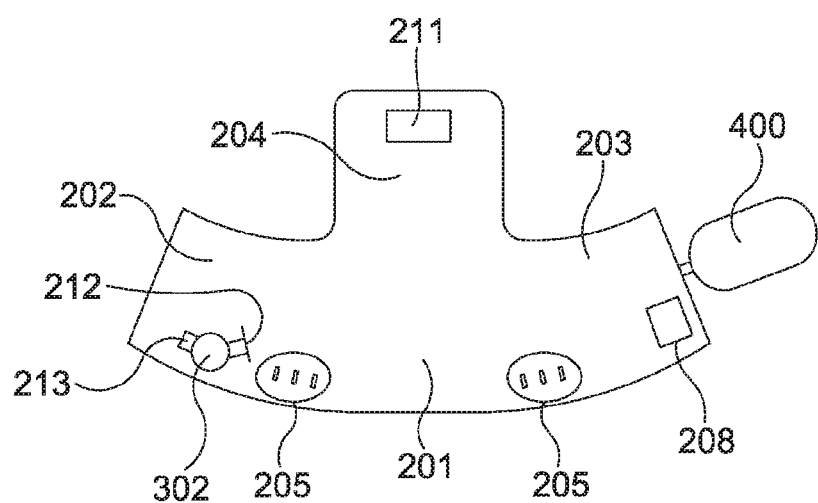
FIG. 5 is a view of the hat of FIG. 4 in an unfolded configuration from the interior side of the hat.
Figure 11:
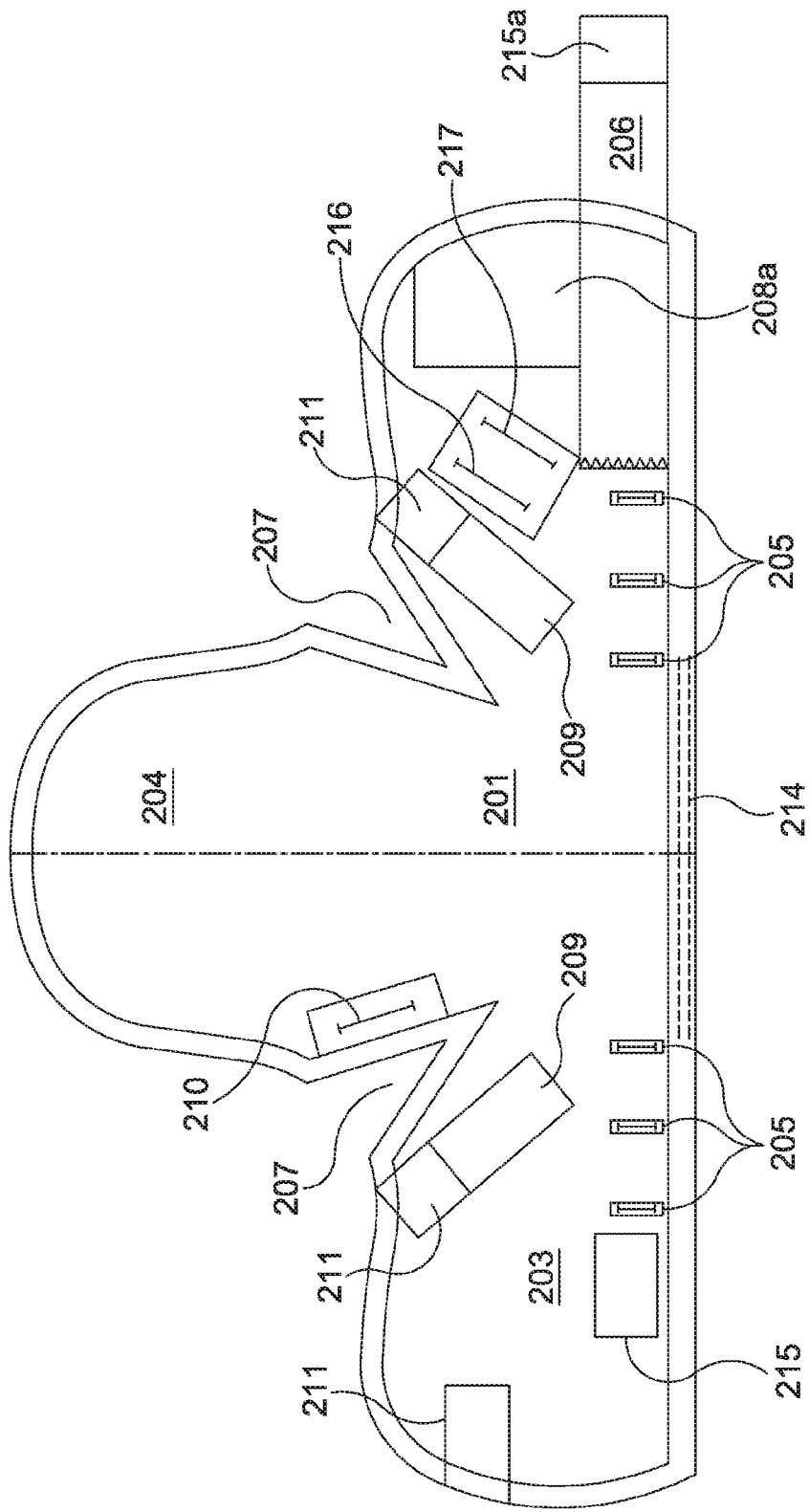
FIG. 11 is a diagram of the outer side of a hat according to the further embodiment

The top flap 204 in each example embodiment is attached to the central portion 201 of the hat (although in other embodiments, could conceivably be attached to the first or second portion 202, 203), and is operable to cover the top of a neonate's head when the hat 200 is worn. The top flap 204 includes a second fastener 211, which conveniently comprises at least one hook portion. FIGS. 4 and 5 show an embodiment with a single central hook portion; FIGS. 8 and 9 show an embodiment with three hook portions, spaced apart along the inner edge of the top flap 204, and FIGS. 10 and 11 show an embodiment with three loop portions, spaced apart along the inner edge of the top flap 204. FIGS. 12 and 13 show an embodiment in which the second fastener 211 comprises two loop portions, on either side of the top flap 204. The loop portions of the second fastener 211 may be provided on protruding "ears" that extend outward from the top flap 204.

The second fastener 211 may further comprise complementary hook/loop portions, positioned on at least one of the first and second portions 202, 203, so as to secure the top flap 204 over the top of the head of the neonate 120, as shown in FIGS. 9 and 11 and FIGS. 12 and 13.

A hat 200 according to an embodiment may be advantageous over prior art neonatal hats, independent of it including any physiological sensor. An unfolded hat arrangement that is subsequently wrapped around a neonate's head is easier to put on. As illustrated in FIG. 6, the neonate can simply be placed on the unfolded hat, then the hat wrapped around the neonate's head to provide an accurate and proper fit. The first fastener 208 may accommodate straightforward and simple adjustment of the size of the head, as it is being put on, in contrast to hats that do not unfold, where an incorrect judgement about the appropriate size hat can be remedied only by trying a different sized hat. In addition, the top flap 204 provides fast and easy access to the top of the neonate's head, enabling cranial ultrasound procedures to be performed without the need to disturb the hat 200.

The hat 200 shown in FIGS. 4 and 5 includes an optical physiological sensor 300 (and the hats shown in FIGS. 8 to 13 are likewise for use with an optical physiological sensor). The physiological sensor 300 comprises a lead portion 301, sensor portion 302, and module portion 305 (the module portion shown in FIG. 10, but hidden by the readout module 400 in FIGS. 4 and 5). The sensor portion 302 of the physiological sensor 300 is held in position by the lead portion 301 being routed through the hat 200. In these example embodiments, the sensor portion 302 is further held in place using a tang 303 of the sensor 300 that is received in a hole in the hat 200, but this is not essential (e.g. alternative further support means may be provided for the sensor portion 302).

The hat 200 may comprise an inner and outer fabric ply. In some embodiments a first outer hole 210 may be provided through the outer ply (and not the inner ply) in the central portion 201, and a first inner hole 212 may be provided through the inner ply (and not the outer ply) in the first portion 202. The first inner and first outer hole are thereby configured to allow the lead 301 of an optical physiological sensor 300 to be supported/concealed between the inner and outer ply, from a suitable location for the sensor portion 302 of the sensor 300, to a location that is suitable for the lead 301 to exit the hat (e.g. in the central portion 201, the first portion 202, or the second portion 203).

A second inner hole 213 may be provided spaced apart from the first inner hole 212 (as shown in FIGS. 5 and 9), by a distance sufficient to accommodate the sensor portion 302 of the sensor 300. The distance between the first inner hole 212 and second inner hole 213 is preferably between 0.5 cm and 3 cm. The second inner hole 213 is arranged to receive a tang 303 of the sensor 300, so as to support the sensor portion 302 in the proper position within the hat 200. In other embodiments, alternative means may be used to secure the sensor portion 302 in position (e.g. a hook and loop fastener, or magnetic elements).

As shown in FIGS. 8 to 11, further outer holes may be provided to enable at least part of the sensor 300 to be removed from the hat 200 without disturbing the neonate 120. A second outer hole 216 and third outer hole 217 may be provided, between the first inner hole 212 and the first outer hole 210, where the lead 301 respectively enters and exits the gap between the inner and outer ply of the hat 200. The lead 301 may thereby be routed to the exterior of the hat 200 between the second and third outer holes 216, 217 on its way to the first outer hole 210. In addition to providing further support for the lead portion 301, this arrangement allows the lead 301 to be conveniently cut while the hat is being worn. Once the lead 301 is cut, the part of the lead 301 that is attached to the module portion 305 can easily be withdrawn from the hat 200 by gently pulling it. This then allows the sensor portion 302 to be removed thereby limiting the time that the sensor is in contact with the skin.

The second and third outer holes 216, 217 are preferably positioned on an exterior part of the first portion 202 that is not overlapped by the second portion 201 when the hat 200 is worn. The second and third outer holes 216, 217 are preferably closer to the first inner hole 212 than the first outer hole 210, so as to reduce the length of lead 301 remaining in the hat 200 if the lead 301 is cut between the second and third outer holes 216, 217. The lead 301a between the second and third outer holes 216, 217 can be seen in FIG. 10.

In more general terms, the hat 200 may be provided with a first sensor hole and second sensor hole for retaining the sensor within the hat 200. In the examples of FIGS. 8 to 11, the first and second sensor hole are the first and second inner hole 212, 213, which are configured to receive the lead 301 and tang 303 of the sensor. In the example of FIGS. 12 and 13, the first and second sensor holes 222, 223 are through holes in the single-play material 231, but not through the hook accepting second-ply 232. The distance between the first and second sensor hole 222, 223 may be between 0.5 cm and 3 cm. A first outer hole 210 may be provided in the hook accepting outer ply 232 to allow a sensor lead to exit the space between the inner ply (e.g. SPL) and the outer ply. Each of the first sensor hole 222, second sensor hole 223, and first outer hole 210 may be arranged on a substantially straight line on the fabric hat material (before darts 207 are sewn).

In FIGS. 8 and 9, dotted lines indicate stitching, dot-dash lines indicate overlocking and the solid line represents the outline. Single layer holes (through either the inner or outer ply only) are indicated by a concentric rectangles with a dotted outer rectangle, and double layer holes (through both inner and outer ply) are indicated by a solid line concentric rectangles. The rim 214 of the hat is indicated in FIGS. 8 to 11.

FIGS. 12 and 13 show an embodiment in which a single ply material is used to form the hat (such as a spun-bond-laminate, or SBL material). The outline of the single-ply material 231 is shown in FIGS. 12 and 13. A further layer 232 (e.g. a second ply) of hook accepting material may be attached to the single-ply material 231, in areas at which a loop fastener is intended to be attachable. In the embodiment of FIGS. 12 and 13, the completed hat 200 comprises a substantially continuous region of hook accepting material along the rim of the hat, for removably adhering to hook portions of the first and second fasteners 208, 211 and of the CPAP loop elements 209. The region of hook accepting material 232 along the rim of the hat provides a wide range of hook accepting area, improving the adjustability of the hat. The hook accepting material 232 may comprise multiple layers laminated together, for example a cotton/foam/velour layer structure, in which the velour is hook accepting.

The hat 200 may comprise at least one dart 207, to improve the fit of the hat on the head of a neonate particularly around the curvature of the occiput 120. There is preferably a dart 207 between the central portion 201 and the first portion 202, and between the central portion 201 and the second portion 203. The darts 207 preferably extends from the top edge of the hat (opposite the rim 214), to around halfway between the top edge and the rim 214. The darts 207 may be non-parallel, for example being angled so that the gap between them is smaller nearer to the rim 214. In FIGS. 8 and 9 the darts 207 are shown in a closed configuration, and in FIGS. 10 and 11 the darts 207 are shown before their edges have been drawn together. A dart 207 may be provided in the central portion 201, as shown in the embodiment of FIGS. 12 and 13. Drawing the darts 207 closed may comprise sewing together points 227 of the hat 200, which may be inward from the edge of the fabric 231.

The hat 200 is provided with a number of features for securing/supporting CPAP apparatus or an intubation tube. The hat may include at least one of a strap 206, loop elements 209, and eyelets 205, for this purpose.

A plurality of eyelets 205 are provided in each of the first and second portion 202, 203, on either side of the central portion 201 of the hat 200. Three eyelets 205 may be provided on each of the first and second portion 202, 203, which enables lacing for a CPAP mask (or similar) to be secured at different locations to the hat 200, providing for an improved fit over a broader range of head shapes and sizes.

A strap 206 may be attached to the first portion 202 (as shown in FIGS. 10 and 11) or the second portion 203 (as shown in FIGS. 8 and 9) at one end (by sewing). A strap fastener 215 may be provided for securing the other end of the strap 206 to the first portion 202 or the second portion 203. The strap fastener 215 may comprise a hook and loop fastener. The strap fastener 215 may comprise a hook portion 215a at the end of the strap 206, and a corresponding loop portion on the exterior of the second portion 203, as shown in FIG. 9. Alternatively, the strap fastener 215 may comprise a loop fastener 215a on the strap 206, and a hook fastener 215 on the first or second portion 203 (as in the embodiment of FIGS. 10 and 11). In the embodiment of FIGS. 12 and 13 the CPAP strap 206 may be a separate part that comprises hook fasteners at each end, which is attachable to the hook accepting fabric portion 231.

The loop element 209 may comprise a loop (or hook) region of hook and loop fastener material, so that a strip of hook material may be adhered to the loop element to secure a tube adjacent to the loop element (such a hook region 219 being shown in FIG. 12). A loop element or region 209 is disposed on the exterior side, or at the edge of each the first and second portions 202, 203. The loop region 209 may comprise part of a larger continuous region of hook accepting material (e.g. as described above with reference to FIGS. 12 and 13). The strap 206 and/or the strips of material for adhering to the loop element 209 may comprise an elastic fabric material. The strap 206 and/or loops 209 may comprise a friction enhancing inner surface region, which may comprise a material such as silicone rubber.

All material that is to be sewed to the main hat material 200 is preferably of a form that is compatible.

Figure 14:
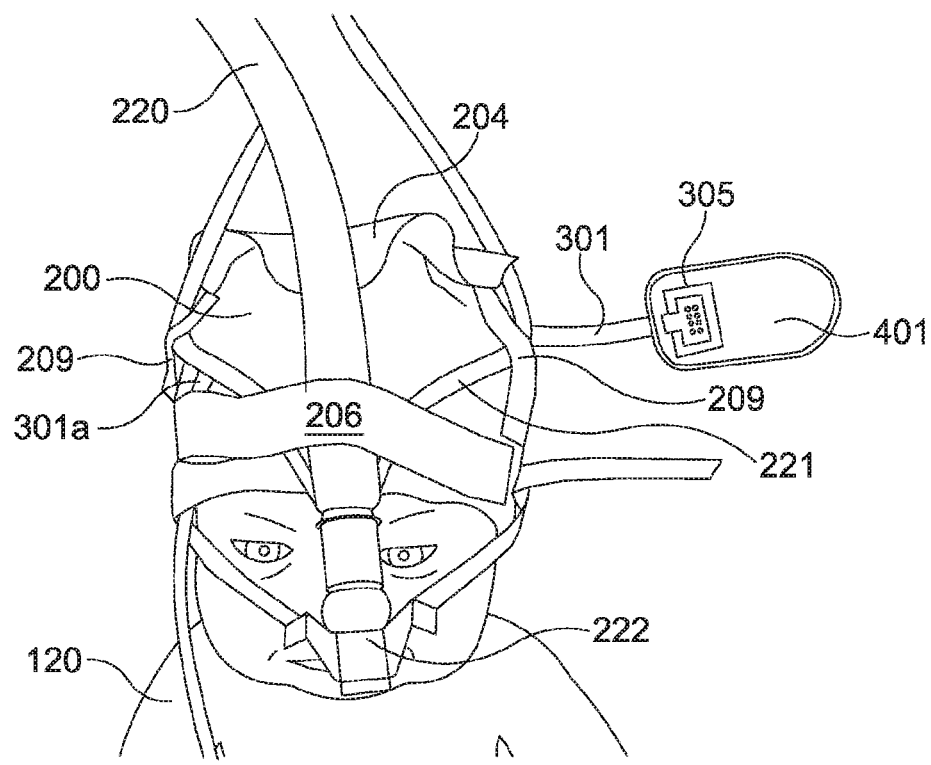
FIG. 14 is a view of a hat according to an embodiment being worn by a neonate, and further including a CPAP mask and associated tubes.

FIG. 14 illustrates the strap 206, loop elements 209 and eyelets 205 in use, with a CPAP mask 220 supported in the correct position on a neonate by the hat 200. The CPAP exhaust tube 220 is supported under the strap 206, and the two supply tubes are supported by adhering a hook fastener strip to each loop element 209. The strap/lacing of the mask is threaded through an appropriate pair of eyelets 205 at each of the first and second portion 202, 203.

The sensor 300 is shown in FIGS. 7 and 15 to 17, and comprises a flexible circuit board that includes the sensor portion 302, lead portion 301 and module portion 305. Using a single flexible circuit board to define all of these parts of the sensor 300 eliminates connections between a sensor portion and lead, and between a lead and a subsequent connector, which are potential points of failure. Furthermore, this approach results in a very low profile arrangement: the thickness of the flexible circuit board may be less than 0.5 mm.

Figure 15:
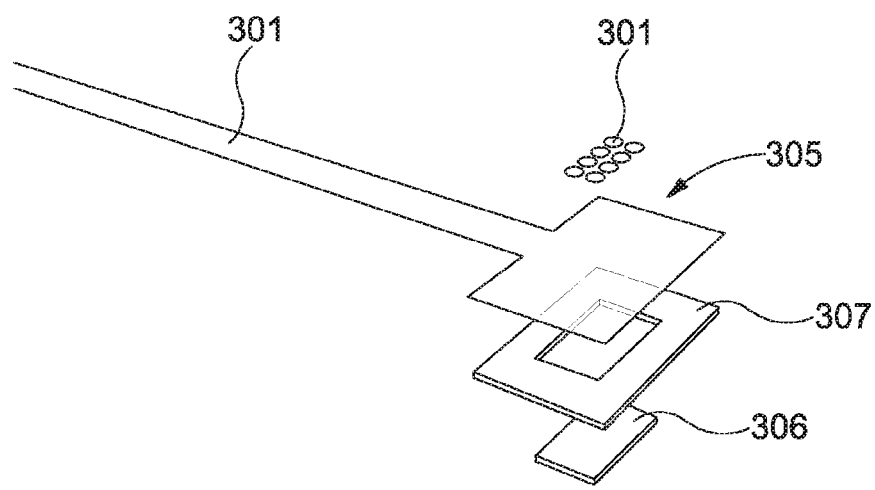
FIG. 15 is an exploded diagram of a module portion of a pulse oximeter according to an embodiment.

FIG. 15 shows the construction of the module portion 305 of the sensor 300 in more detail. The module portion 305 is arranged to engage with the readout module 400 and to provide an electrical connection between the sensor 300 and readout module 400.

The module portion 305 comprises: contacts 301, conducting tracks (not shown); a ferromagnetic element 307 and a rigidiser 306. The contacts 301 are exposed conducting regions that are connected to conducting tracks of the lead 301, that are in turn connected to the light emitter 310 and light detector 311 at the sensor portion 302. The ferromagnetic element 307 is a substantially planar sheet of a magnetic material such as steel. The rigidiser 306 is a substantially planar element (e.g. a plate) that is stiffer than the flexible circuit board, and which supports the contacts 301 from behind. The rigidiser 306 may fit in a recess or through hole in the ferromagnetic element 307.

Figure 16:
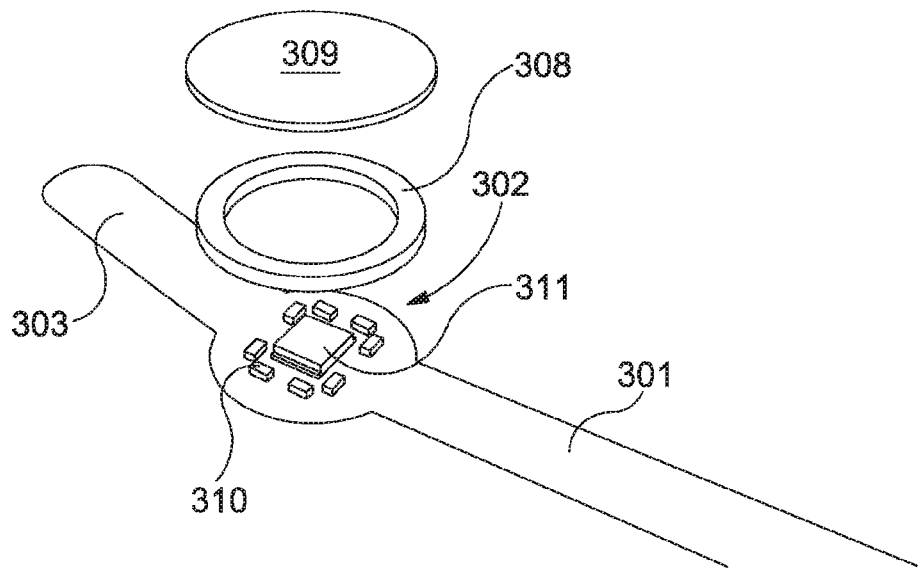
FIG. 16 is an exploded diagram of a sensor portion of an optical physiological sensor according to an embodiment.

FIG. 16 shows the sensor portion 302, which comprises the light emitter 310, light detector 311, compressible element 308 and transparent element 309. The light emitter 310 may comprise a plurality of light emitting elements (such as light emitting diodes or LEDs). There may be more than one colour LED (e.g. infra-red, green, red etc). The light detector 311 may comprise a photodiode (or an array of photodiodes, or a multi-pixel camera chip not necessarily operating in the visible region). Where the light detector 311 comprises a plurality of light detecting elements, at least some of the light detecting elements may be configured with a different spectral response to the others (e.g. using a spectral filter), so that additional information may be obtained at the same time from more than one colour light emitter. Alternatively independent component analysis can be implemented on multi-detectors to separate out orthogonal components.

In the example shown, the light emitter 310 comprises a plurality of discrete LEDs, arranged around a central light detector 311. In other embodiments the light detector 311 and light emitter 310 may be disposed in a single package. In some embodiments the light emitter 310 and detector 311 may be separated by a baffle, which prevents light from the emitter 310 being directly detected by the detector 311. Or the LED's may be positioned at a lower level than the photodetector (relative to the transparent element 309) so that no direct light shunting occurs.

The compressible element 308 is formed of an elastic material, such as a closed cell foam, so that the optically transparent element 309 can conform to the skin of the neonate 120, minimising the potential for a pressure injury. The transparent element 309 may also be relatively soft (e.g. compared to glass or polycarbonate), for instance being formed from optically clear silicone. The addition of an adhesive or tacky layer to the outer side of the transparent element 309 may help the sensor portion 302 to remain in contact with the skin and reduce slippage across the skin. Cross-polarisers can be placed between layers 308 and 309 to reduce internal reflection shunting.

In some embodiments, the sensor portion 302 may comprise at least one electrode for making electrical contact with the skin of the neonate, for example to perform an ECG measurement. The lead 301 may comprise at least one branch for connecting further electrodes at different positions on the neonate (for example, not on the head). The electrodes may be of any suitable type, including (but not limited to) wet electrodes, electrodes configured for capacitive coupling to the skin, and electrodes configured for connection to skin via a coupling gel (e.g. a hydrogel). The tang 303 extends away from the sensor portion 302, in a different direction to the lead 301. In the example embodiment, the tang is at an angle of approximately 145 degrees to the lead 301, which results in the tang 303 being approximately parallel with the rim 314 of the hat 200 when the sensor portion 302 is between the first and second inner hole 212, 213. In some embodiments the tang 303 may extend away from the sensor portion at around 180 degrees from the lead 301.

Figure 17:
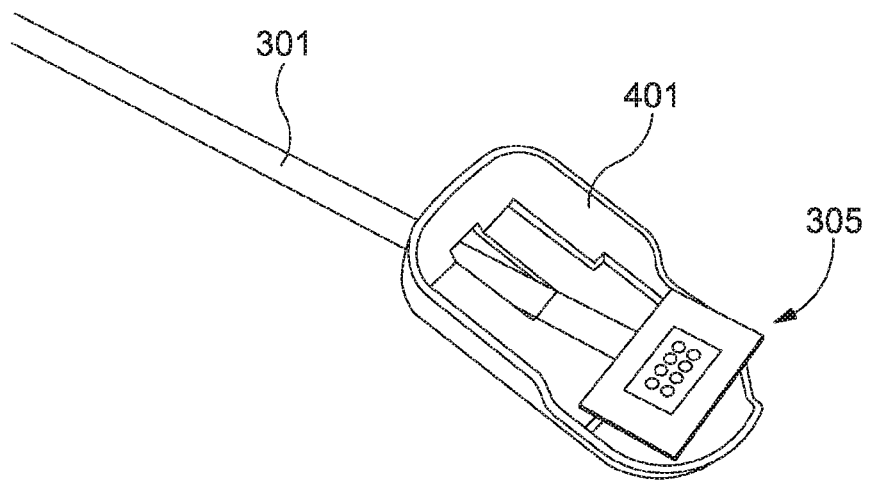
FIG. 17 is a view of the module portion of the optical physiological sensor of FIG. 14, with the module portion partly inserted into a cradle of a readout module.
Figure 18:
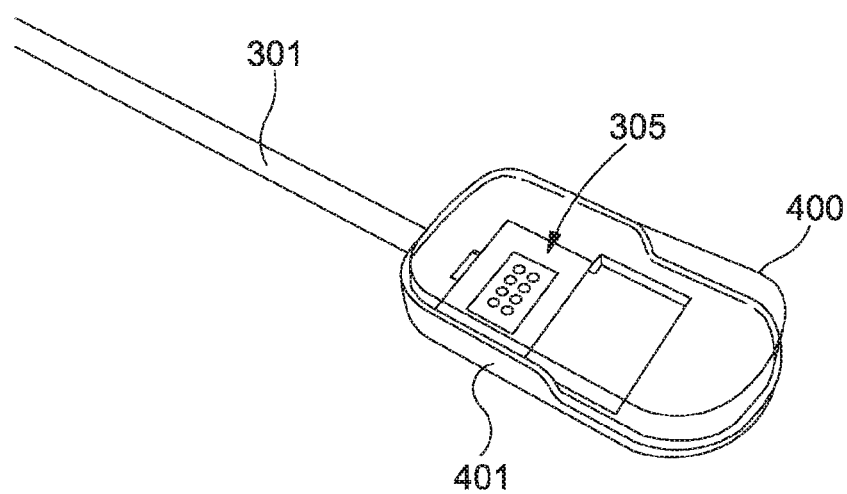
FIG. 18 is a view of the cradle of FIG. 16 with the module portion fully engaged with the cradle, and with a readout module housing engaged with the cradle.

FIGS. 17 and 18 illustrate how the module portion 305 of the sensor is connected to the readout module 400. A cradle 401 is provided, which assists in engaging and maintaining engagement between the module portion 305 and the readout module 400. The cradle 401 is configured to receive part of the housing base 402b, and has a wall that guides the housing into the proper location in the cradle 401. The cradle 401 further includes a slot in the base thereof, through which the module portion 305 of the sensor 300 can be inserted. The module portion 305 may subsequently be located within a slot of the cradle 401, with the lead portion 301 exiting the cradle 401 through the slot 401. The cradle 401 may be configured to require the cradle 401 to be initially moved relative to the module portion 305 in the direction of the lead 301 to disengage the module portion 305 from the slot. This helps to prevent the module portion 305 being disturbed in use, and helps maintain a secure connection between the readout module 400 and sensor 300.

As shown in FIG. 18, when the readout module 400 is received within the cradle 401, the magnets of the readout module 400 may align with the ferromagnetic element 307 of the module portion 305, which urges the connector 408 into electrical contact with the contacts 304.

Figure 19:
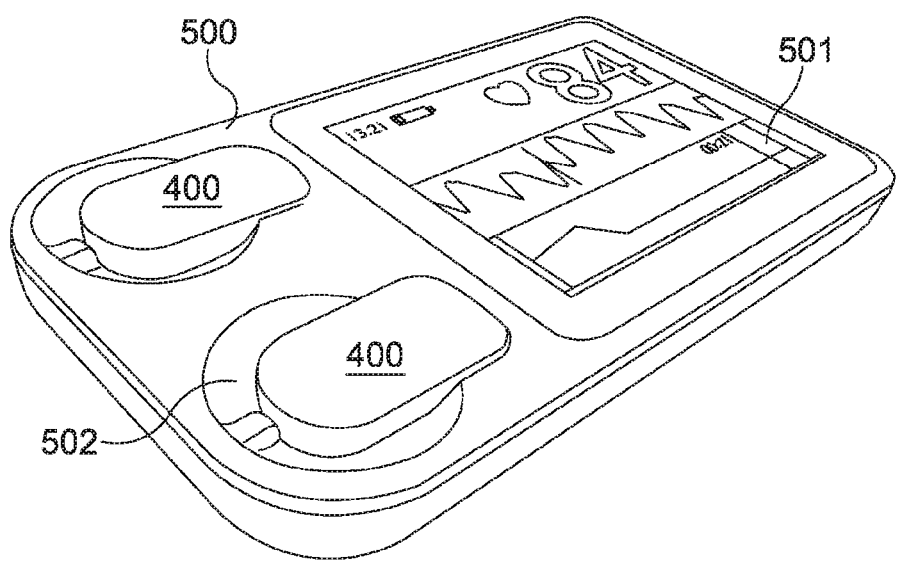
FIG. 19 is view of a receiving station according to an embodiment, with a first and second readout module inserted in a first and second docking portion of the receiving station.

FIG. 19 shows a receiver station 500, comprising a display 501 and a pair of docking portions 501.

The display 501 is for indicating the heart rate and other physiological variables of the neonate 120, based on data transmitted to the receiver station 500 wirelessly by the readout module 400. The receiver station 500 may be configured to show a time history of the pulse rate or blood oxygen saturation as a graph, the instantaneous pulse rate (e.g. as number indicating beats per minute), the breathing rate, an indication of battery status (e.g. for a charging module 400, or the transmitting module 400), the time, or any other information that may be appropriate.

Each docking portion is configured to receive a readout module 400. The receiver station 500 may be configured to charge each readout module 400 via each docking portion 502.

The receiver station (500) may contain adequate storage to collect all data from a recording session in a non-volatile format. This is useful for training purposes, medico-legal reasons and clinical records for example. Data can be accessed by removing the internal storage card, by wired or wireless connections.

Figure 20:
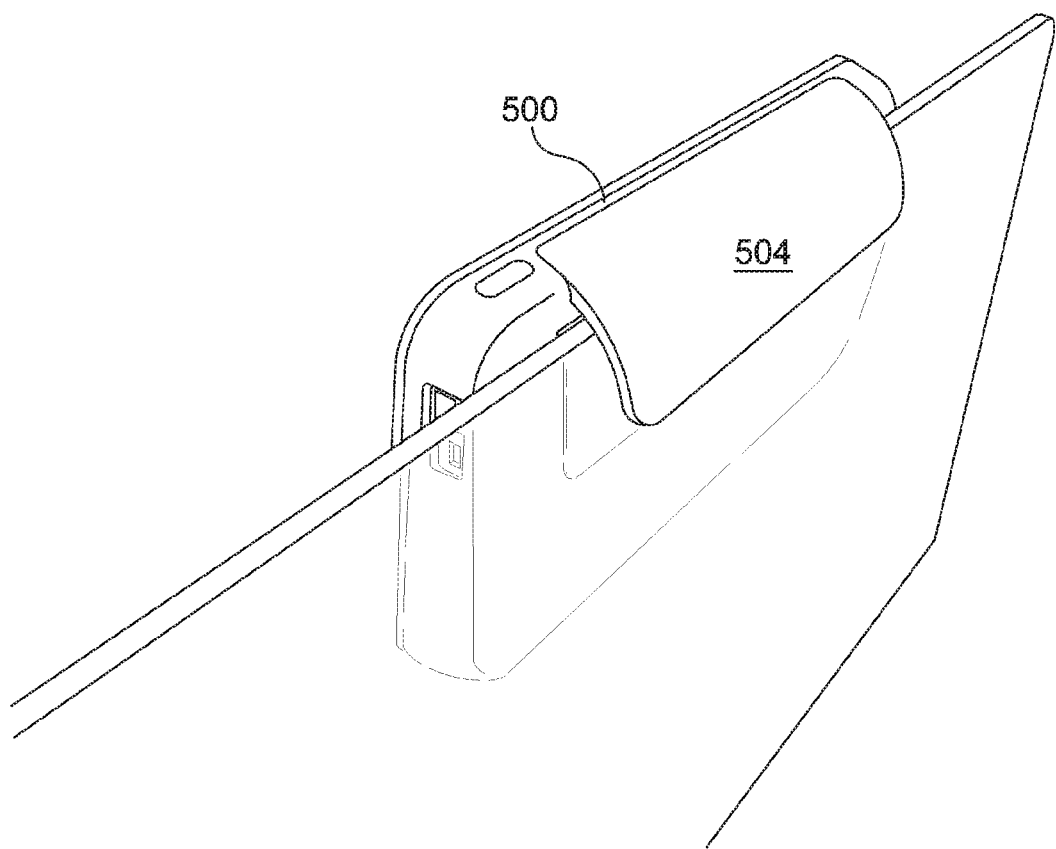
FIG. 20 is a view of the receiving station of FIG. 19 hanging from an edge of a resuscitaire.

The receiver station 500 may further comprise a hanger 504, by which the receiver station 500 can be secured to a sidewall of a resuscitaire, as shown in FIG. 20.

The embodiments described above address a number of potential applications. In one use case, a clinician may identify a need for heart rate monitoring of a neonate, following an assessment of the neonate on delivery.

A prepared hat 200 may be positioned on a resuscitaire 110 in the unfolded configuration. The prepared hat 200 includes a sensor 300, as described above. The sensor 300 may be already connected to a readout module 400, which may already be in communication with the receiving station 500.

The neonate may be placed with their head on the central portion 201 of the hat 200, and the hat 200 wrapped around the head, so that the sensor portion 302 contacts the head (e.g. forehead) of the neonate 120. If a readout module 400 is not already engaged with the module portion 305, a readout module 400 may be taken from the docking portion 502 and engaged with the readout module 400 (e.g. by placing it in cradle 401).

The readout module 400 may subsequently transmit data derived from the output of the sensor 300 to the receiver station 500. As already discussed, the processing of the data from the sensor 300 to determine heart rate (and/or blood oxygen saturation, breathing rate etc) may take place at the readout module 400 and/or the receiver station 500. The receiver station subsequently displays the heart rate and/or blood oxygen saturation (e.g. an instantaneous indication and/or a time history in the form of a graph).

The hat 200 may be kept on the head of the neonate 120 while any treatment to remedy poor respiratory function and/or heart rate etc is given. An accurate time history of the heart rate etc made available at the resuscitaire will assist the treating clinician in determining whether their actions are having the desired effect. If it is determined that the neonate 120 needs to be transferred to a neonatal intensive care unit (NICU), the physiological signals of the neonate can continue to be monitored during transit of the resuscitaire to the NICU.

Once the neonate is stabilised, or has arrived at the NICU, the hat 200 may be removed, or the sensor removed from the hat 200. Removing the sensor can be achieved by cutting the lead 301 between the second and third outer hole, and then pulling the lead from the hat 200. In some embodiments (such as that of FIGS. 12 and 13), removing the sensor may comprise cutting the lead 301 outside the hat (e.g. not between second and third outer holes). The sensor element can subsequently be removed by briefly lifting the first portion 202 and detaching the sensor portion 302 from the interior. Each hat 200 and sensor 300 may be a single-use disposable item.

In another use-case, the hat may be applied as a matter of routine to each newborn, so that the physiological signals can be assessed to ensure that they are healthy before they leave the delivery suite.

A further use-case is for babies older than 4 weeks (e.g. for babies up to 6 months or even 1 year old), for instance to monitor for the onset of SIDS (sudden infant death syndrome). Although a hat for a neonate has been described, the same principles are also applicable to a hat for an older baby.

One issue present in the delivery room is the availability of ECG equipment for newborn monitoring. A device that is being used to monitor the fetal ECG could be transferred to continue to monitor the newborn ECG, simply by swapping the data receiving device from the electrodes used to monitor the mother and/or fetus to the electrodes on the sensor portion that are connected to the newborn baby (e.g. in the hat). Using the same interface to the cardiotocogram printout mechanism could allow for data recording.

A number of examples have been described, which are not intended to limit the scope of the invention, which is limited only by the appended claims.

What is claimed is:

1. A hat for a neonate comprising:
    a central portion, a first side portion and second side portion attached to opposite sides of the central portion, a first fastener;
    a top flap and a second fastener;
    wherein the hat has an unfolded configuration in which the first and second portions extend away from each other from the central portion in opposite directions; and a worn configuration in which the hat wraps a neonate's head with the central portion in contact with the back of the neonate's head, the first portion wrapped around a first side of the neonate's head and the second portion wrapped around a second side of the neonate's head;
    the first and second portions being configured to be fastened together in the worn configuration by the first fastener so that the first portion, central portion and second portion together define a hat rim encircling the neonate's head; and
    the top flap is configured to cover the top of the neonate's head in the worn configuration, with the top flap being configured to be fastened to at least one of the first, central and second portions by the second fastener wherein the hat covers most of the top of the neonate's head in the worn configuration;
    the hat further comprising an optical physiological sensor carried by the first portion, the physiological sensor held in contact with the forehead of the neonate by the first portion, the physiological sensor comprising:
        a flexible circuit board, a light emitter, and a light detector; the flexible circuit board having:
            a sensor portion to which the light emitter and light detector are connected;
            a module portion including contacts for electrically connecting the light emitter and light detector to a removable readout module; and
        an elongate lead portion between the sensor portion and module portion.

2. The hat of claim 1, wherein the hat is substantially T-shaped when in an unfolded configuration, with the top flap being connected to the central portion; and wherein the first and second portions are configured to overlap on the neonate's forehead when fastened together by the first fastener.

3. The hat of claim 1, wherein the first fastener and/or the second fastener comprise a hook and loop fastener.

4. The hat of claim 1, further comprising a strap for supporting a tube adjacent to the neonate's forehead when the first, central and second portions encircle the neonate's head.

5. The hat of claim 4, wherein the strap:
i) comprises an elastic fabric material;
ii) comprises a strap fastener, for fastening the strap to at least one of the first and second portions;
iii) is fixed at one end to one of the first or second portion, and the other end is securable to the other of the first or second portions using the strap fastener; and/or
iv) comprises a friction enhancing lining on an inner surface thereof.

6. The hat of claim 1, comprising a first plurality of eyelets in the first portion adjacent to the hat rim, and a second plurality of eyelets in the second portion adjacent to the hat rim, the first and second plurality of eyelets for securing a CPAP mask to the neonate's face using CPAP cords that thread into the eyelets, the plurality of eyelets in each of the first and second portion providing a range of CPAP mask securing locations, and/or
at least one hook or loop element against which a tube may be supported adjacent to the exterior of the hat.

7. The hat of claim 1, comprising a first dart between the first and central portion and a second dart between the second and central portion;
wherein the first and second dart extend substantially toward the rim from a top edge of the hat, the top edge being on the opposite side of the hat to the hat rim.

8. The hat of claim 1, wherein the second fastener comprises a plurality of fastening locations spaced around the perimeter of the top flap.

9. The hat of claim 1, wherein the first, second, and central portions, and the top flap, are substantially formed from a fabric material, and the fabric material is stretchable substantially in one direction only.

10. The hat of claim 9, wherein the direction is along the circumference.

11. The hat of claim 1, wherein the first, second, and central portions, and the top flap, are substantially formed from a fabric material, and wherein:
the fabric has at least an inner ply and an outer ply; and
the hat further comprises an inner hole through the inner fabric ply at a first location and an outer hole through the outer fabric ply at a second location; the inner and outer hole allowing an optical physiological sensor lead to be threaded through a space between the inner and outer plies between the inner and outer holes.

12. The hat of claim 11, wherein:
i) the inner hole is a first inner hole, and the hat further comprises a second inner hole through the inner fabric ply, spaced apart from the first inner hole by 0.5 cm to 3 cm; and/or
ii) the outer hole is a first outer hole, and the hat further comprises a second and third outer hole disposed between the inner hole and the first outer hole.

13. The hat of claim 1, wherein the sensor portion comprises a transparent element covering the light emitter and light detector the transparent element comprising a region that is adhesive or tacky to skin.

14. The hat of claim 1, wherein the sensor portion further comprises at least one electrode for making an electrical connection to the skin of the neonate.

15. The hat of claim 1, wherein the light emitter comprises a first light emitting element with a first output wavelength, and a second light emitting element with a second, different output wavelength.

16. The hat of claim 1, wherein the flexible circuit board includes a tang extending away from the sensor portion in a different direction to the lead.

17. The hat of claim 16, wherein the tang:
i) is an elongate member and the tang extends away from the sensor portion at an angle of between 170 and 190 degrees from the lead; and/or
ii) comprises at least one lateral projection or recess configured to assist in preventing withdrawal of the tang through a hole in the hat.

18. The hat of claim 1, wherein the width of the lead is less than 1 cm and/or the thickness of the lead is less than 0.5 mm.

19. The hat of claim 1, wherein the module portion comprises:
a substantially rigid planar element for supporting the contacts; and/or
a ferromagnetic element.

20. The hat of claim 1, wherein at least part of the elongate lead portion of the optical physiological sensor is disposed between an inner and an outer ply of the hat and the sensor portion is supported by the hat at an inner surface of the hat near the rim of the first portion or the second portion, such that the sensor portion is positioned on a neonate's forehead when the hat is worn.

21. The hat of claim 20, wherein the hat comprises an inner hole through the inner fabric ply at a first location and an outer hole through the outer fabric ply at a second location; the inner and outer hole allowing an optical physiological sensor lead to be threaded through a space between the inner and outer plies between the inner and outer holes, and the optical physiological sensor includes a tang extending away from the sensor portion in a different direction to the lead, and the sensor portion is supported between the first inner hole and the second inner hole, the first inner hole receiving the elongate lead portion, and the second inner hole receiving the tang.

22. The hat of claim 21, wherein the outer hole is a first outer hole, and the hat further comprises second and third outer holes, the elongate lead portion is threaded between the second and third outer holes, so as to enable the lead portion to be cut between the second and third outer holes while the hat is worn, so that the sensor portion can subsequently be withdrawn from the hat.

* * * * *